US009845480B2

(12) United States Patent
Eberwine et al.

(10) Patent No.: US 9,845,480 B2
(45) Date of Patent: Dec. 19, 2017

(54) TRANSCRIPTOME TRANSFER PRODUCES CELLULAR PHENOTYPE CONVERSION

(71) Applicant: The Trustees of the University of Pennsylvania, Philadelphia, PA (US)

(72) Inventors: James Eberwine, Philadelphia, PA (US); Jai-Yoon Sul, Cherry Hill, NJ (US); Tae Kyung Kim, Wynnewood, PA (US); Vickas Patel, Berwyn, PA (US)

(73) Assignee: THE TRUSTEES OF THE UNIVERSITY OF PENNSYLVANIA, Philadelphia, PA (US)

(*) Notice: Subject to any disclaimer, the term of this patent is extended or adjusted under 35 U.S.C. 154(b) by 0 days.

(21) Appl. No.: 14/880,737

(22) Filed: Oct. 12, 2015

(65) Prior Publication Data
US 2016/0046958 A1    Feb. 18, 2016

Related U.S. Application Data

(63) Continuation of application No. 13/186,232, filed on Jul. 19, 2011, now Pat. No. 9,157,066, which is a continuation-in-part of application No. 12/755,277, filed on Apr. 6, 2010, which is a continuation-in-part of application No. 12/086,471, filed as application No. PCT/US2006/047480 on Dec. 12, 2006.

(60) Provisional application No. 60/749,941, filed on Dec. 13, 2005, provisional application No. 61/167,286, filed on Apr. 7, 2009.

(51) Int. Cl.
C12N 15/85    (2006.01)
A61K 31/713   (2006.01)
A61K 45/06    (2006.01)
C12N 5/079    (2010.01)
C12N 5/077    (2010.01)
A61K 48/00    (2006.01)

(52) U.S. Cl.
CPC ............ C12N 15/85 (2013.01); A61K 31/713 (2013.01); A61K 45/06 (2013.01); C12N 5/0622 (2013.01); C12N 5/0657 (2013.01); A61K 48/00 (2013.01); C12N 2501/998 (2013.01); C12N 2506/00 (2013.01); C12N 2506/08 (2013.01); C12N 2506/1307 (2013.01)

(58) Field of Classification Search
None
See application file for complete search history.

(56) References Cited

U.S. PATENT DOCUMENTS

| 3,711,262 A | 1/1973 | Keck et al. |
| 5,034,506 A | 7/1991 | Summerton et al. |
| 5,330,467 A | 7/1994 | Abela |
| 5,891,634 A | 4/1999 | Petri, Jr. et al. |
| 6,458,594 B1 | 10/2002 | Baszczynski et al. |
| 6,753,161 B2 | 6/2004 | Koller et al. |
| 6,973,245 B2 | 12/2005 | Bocanegra et al. |
| 2004/0180430 A1 | 9/2004 | West et al. |
| 2004/0235175 A1 | 11/2004 | Gaudernack et al. |
| 2009/0068742 A1 | 3/2009 | Yamanaka |
| 2011/0033934 A1 | 2/2011 | Eberwine et al. |
| 2012/0129261 A1 | 5/2012 | Eberwine et al. |
| 2012/0135493 A1 | 5/2012 | Eberwine et al. |
| 2012/0178167 A1 | 7/2012 | Eberwine et al. |

FOREIGN PATENT DOCUMENTS

| EP | 0137504 | 1/1991 |
| EP | 1 083 232 A1 | 9/1999 |
| EP | 1 391 503 A1 | 12/2002 |
| EP | 1 270 732 | 1/2003 |
| EP | 1225228 | 8/2005 |
| JP | 2005-168495 | 6/2005 |
| WO | 96/18741 | 6/1996 |
| WO | 99/14346 | 3/1999 |
| WO | 01/75164 | 10/2001 |
| WO | 02/090555 | 11/2002 |
| WO | 03/079883 | 10/2003 |
| WO | 2005/044367 | 5/2005 |
| WO | 2006/059084 | 6/2006 |
| WO | 2007/047766 | 4/2007 |
| WO | 2007/084228 | 7/2007 |

OTHER PUBLICATIONS

U.S. Appl. No. 60/726,915, filed Oct. 14, 2005, Hu.
Guo Y. et al., "Laser-mediated gene transfer in rice", *Physiologia Plantarym*, 93 (19-24), 1995.
Palumbo G. et al., "Targeted gene transfer in eukaryotic cells by dye-assisted laser optoporation", *Journal of Photochemistry and Photobiology*, 36(1): 41-46, 1996.
Paterson L. et al., "Photoporation and cell transfection using a violet diode laser", *Optics Express*, 13(2): 595-600, 2005.
Smits E. et al., "RNA-based gene transfer for adult stem cells and T cells", *Leukemia*, 18: 1898-1902, 2004.
Tao W. et al., "Direct gene transfer into human cultured cells facilitated by laser micropuncture of the cell membrane", *Proceedings of the National Academy of Science USA*, 84: 4180-4184, 1987.
Tirlapur U. K. et al., "Targeted transfection by femtosecond laser", *Nature*, 418: 290-291, 2002.
Van Driessche A. et al,, "Messenger RNA electroporation: an efficient tool in immunotherapy and stem cell research", *Folia Histochemica et Cytobiologica*, 43(4): 213-216, 2005.
Zeira E. et al., "Femtosecond Infrared Laser—An Efficient and Safe in Vivo Gene Delivery System for Prolonged Expression", *Molecular Therapy*, 8(2): 342-350, 2003.
Barrett Lindy E. et al., "Region-directed phototransfection reveals the functional significance of a dendritically synthesized transcription factor," Nature Methods, Jun. 2006, vol. 3, No. 6, pp. 455-460.

(Continued)

Primary Examiner — Doug Schultz
(74) Attorney, Agent, or Firm — Riverside Law LLP

(57) ABSTRACT

The present invention includes methods for effecting phenotype conversion in a cell by transfecting the cell with phenotype-converting nucleic acid. Expression of the nucleic acids results in a phenotype conversion in the transfected cell. Preferably the phenotype-converting nucleic acid is a transcriptome, and more preferably an mRNA transcriptome.

19 Claims, 8 Drawing Sheets

(56) References Cited

OTHER PUBLICATIONS

Bolstad et al., 2003, "A comparison of normalization methods for high density oligonucleotide array data based on variance and bias" Bioinfounaties 19:185-193.
Chen, et al., 2005, "Ventilation-synchronous magnetic resonance microscopy of pulmonary structure and ventilation in mice" Magn. Reson. Med. 53: 69-75.
Dang, et al., 2005, "Comparison of histologic, biochemical, and mechanical properties of murine skin treated with the 1064-nm and 1320-nm Nd:YAG lasers" Exp Dermatol. 14: 876-882.
Eberwine et al., 1992, "Analysis of gene expression in single live neurons " PNAS 89: 3010-3014.
Eberwine, et al., 2001, "Analysis of mRNA populations from single live and fixed cells of the central nervous system". Current protocols in neuroscience (editorial board, Jacqueline N. Crawley et al.) Chapter 5, Unit 5.3.
Eberwine, 2001, "Single Cell Molecular Biology" Nat Neurosci. 4:1155-1156.
The Gene Ontology Consortium, 2000, "Gene ontology: tool for the unification of biology," Nature Genet. 25:25-29.
Hanna et al., 2007, "Treatment of sickle cell anemia mouse model with iPS cells generated from autologous skin" Science 318(5858):1920-1923.
Herberholz et al., 2002, "A Lateral Excitatory Network in the Escape Circuit of Crayfish" J Neurosci. 22: 9078-9085.
Huang et al., 2001, "A novel transcription factor inhibitor, SP100030, inhibits cytokine gene expression, but not airway eosinophilia or hyperresponsiveness in sensitized and allergen-exposed rat" Br. J. Pharmacol., 134: 1029-1036.
Huangfu D, et al. (2008) "Induction of pluripotent stem cells from primary human fibroblasts with only Oct4 and Sox2" Nat Biotechnol 26(11):1269-1275.
Kacharmina, et al., 2000, "Stimulation of glutamate receptor protein synthesis and membrane insertion within isolated neuronal dendrites" PNAS, 97:11545-11550.
Kim et al. (2008) "Pluripotent stem cells induced from adult neural stem cells by reprogramming with two factors" Nature 454(7204):646-650.
Maherali et al. (2007) "Directly reprogrammed fibroblasts show global epigenetic remodeling and widespread tissue contribution" Cell Stem Cell 1(1):55-70.
Martinez et al., 2002, "Single-Stranded Antisense siRNAs Guide Target RNA Cleavage in RNAi" Cell 110:563-74.
Mohanty, et al., 2003, "Laser-assisted microinjection into targeted animal cells" Biotechnol. Lett. 25: 895-899.
Nakagawa M, et al, 2008, "Generation of induced pluripotent stem cells without Myc from mouse and human fibroblasts" Nat Biotechnol 26(1):101-106.
Needham-VanDevanter, et al., 1984, "Characterization of an adduct between CC-1065 and a defined oligodeoxynucleotide duplex" Nucleic Acids Res., 12:6159-6168.
Neufeld et al., 1985, "Uptake and subcellular distribution of [3H]arachidonic acid in murine fibrosarcoma cells measured by electron microscope autoradiography" J Cell Biol. 101(2):573-581.
Okita et al., 2007, "Generation of germline-competent induced pluripotent stem cells" Nature 448(7151):313-317.
Roelandse, et al. 2004, "Hypothermia-Associated Loss of Dendritic Spines" J. Neurosci. 24: 7843-7847.
Rowe et al. 2005, "Development of functional neurons from postnatal stem cells in vitro". Stem Cells 23(8):1044-1049.
Schneckenburger, et al., 2002, "Laser-assisted optoporation of single cells" J. Biomed. Opt., 7: 410-416.
Shirahata, et al., 2001, "New technique for gene transfection using laser irradiation" J. Invest. Med., 49: 184-190.
Soughayer, et al., 2000, "*Characterization of Cellular Optoporation with Distance*" Anal. Chem., 72: 1342-1347.
Stadtfeld et al., 2008, "Induced Pluripotent Stem Cells Generated Without Viral Integration" Science 322(5903):945-949.
Stracke et al., 2005, "Optical Nanoinjection of Macromolecules into Vital Cells" J Photochem Photobiol B 81:136-142, Abstract only.
Takahashi et al., 2006, "Induction of pluripotent stem cells from mouse embryonic and adult fibroblast cultures by defined factors" Cell 126(4):663-676.
Tang et al., 2006, "Efficient delivery of small interfering RNA to plant cells by a nanosecond pulsed laser-induced stress wave for posttranscriptional gene silencing," Plant Science 171:375-381.
Tirlapur et al., 2002, "Femtosecond near-infrared laser pulses as a versatile non-invasive tool for intra-tissue nanoprocessing in plants without comprising viability," The Plant Journal: For Cell and Molecular Biology, 31(3): 365-374.
Valles et al., 1997 "Ethanol exposure affects glial fibrillary acidic protein gene expression and transcription during rat brain development" J. Neurochem 69:2484-2493.
Van Gelder et al., 1990, "Amplified RNA synthesized from limited quantities of heterogeneous cDNA" PNAS 87 (5): 1663-1667.
Wernig et al., 2008, "Neurons derived from reprogrammed fibroblasts functionally integrate into the fetal brain and improve symptoms of rats with Parkinson's disease" PNAS 105(15):5856-5861.
Boczkowski et al., "Induction of Tumor Immunity and Cytotoxic T Lymphocyte Responses Using Dendritic Cells Transfected with Messenger RNA Amplified from Tumor Cells1", *Cancer Research*, 60: 1028-1034, Feb. 15, 2000.
Dannull et al., "Enhanced Antigen Presenting Function of Antigen-Loaded Dendritic Cells Following Cotransfection with OX40 Ligand mRNA", *Proceedings of the American Association for Cancer Research*, 45: 1-2, 2004.
Dannull et al., "Enhancing the Immunostimulatory Function of Dendritic Cells by Transfection with mRNA Encoding OX40 Ligand", *Blood*, 105(8): 3206-3213, Apr. 15, 2005.
Diaz et al., "Sindbis Viral Delivery of EGFP-Dopamine D1 Receptors into Native Neuronal Preparations", Program No. 160.14. 2003 Neuroscience Meeting Planner. New Orleans, LA; *Society for Neuroscience*, 2003, online (Abstract only).
Elango et al., "Optimized Transfection of mRNA Transcribed from a d (A/T) 100 Tail-Containing Vector", *Biochemical and Biophysical Research Communications*, 330: 958-966, 2005.
Fisher et al., "The Transmembrane Domain of Diphtheria Toxin Improves Molecular Conjugate Gene Transfer", *Biochemical Journal*, 321: 49-58, Jan. 1, 1997.
Kalady et al., "Sequential Delivery of Maturation Stimuli Increases Human Dendritic Cell IL-12 Production and Enhances Tumor Antigen-Specific Immunogenicity", *Journal of Surgical Research*, 116: 24-31, 2004.
Kim et al., "Transcriptome Transfer Provides a Model for Understanding the Phenotype of Cardiomyocytes", *PNAS Early Edition*, 2011, retrieved online: www.pnas.org/cgi/doi/10.1073/pnas.1101223108.
Malone et al., "Cationic Liposome-Mediated RNA Transfection", *Proceedings of the National Academy of Science*, 86: 6077-6081, Aug. 1989.
Nair et al., "Induction of Primary Carcinoembryonic Antigen (CEA)—Specific Cytotoxic T Lymphocytes in Vitro Using Human Dendritic Cells Transfected with RNA", *Nature Biotechnology*, 16: 364-369, Apr. 1998.
Rakhmilevich et al, "Eradication of Established Metastatic Murine Tumors Following Particle-Mediated Delivery of IL-12 Gene into the Skin", *Proceedings of the American Association for Cancer Research Annual*, 37: 347, Apr. 20-24, 1996.
Sawai Keisuke et al., "A Novel Method of Cell-Specific mRNA Transfection", *Molecular Genetics and Metabolism*, 64: 44-51, Jan. 7, 1998.
Petrova et al., 2002, "Lymphatic endothelial reprogramming of vascular endothelial cells by the Prox-1 homeobox transcription factor," The EMBO Journal, 21(17: 4593-4599.
Rakhmilevich et al., 2000, Gene Therapy of Cancer: Methods in Molecular Medicine, Ed, W. Walther and U. Stein, Humana Press, Inc. Totowa NJ, vol. 30: 331-344).
Boczkowski et al., 1996, "Dendritic Cells Pulsed with RNA are Potent Antigen-presenting Cells In Vitro and In Vivo." J. Exp. Med, 184: 465-472.

(56) References Cited

OTHER PUBLICATIONS

Izumikawa et al., "Auditory Hair Cell Replacement and Hearing Improvement by Atoh1 Gene Therapy in Deaf Mammals", Nature Medicine, 11(3): 271-276, Mar. 2005.

TRANSCRIPTOME TRANSFER PRODUCES CELLULAR PHENOTYPE CONVERSION

CROSS-REFERENCE TO RELATED APPLICATIONS

This application is a continuation of U.S. application Ser. No. 13/186,232, filed on Jul. 19, 2011, which is a continuation-in part of U.S. patent application Ser. No. 12/755,277, filed on Apr. 6, 2010 which is a continuation-in-part of U.S. application Ser. No. 12/086,471, filed on Jun. 13, 2008, which is the National Stage application of PCT International Application No. PCT/US2006/047480, filed on Dec. 12, 2006, which in turn claims the benefit pursuant to 35 U.S.C. §119(e) of U.S. Provisional Application No. 60/749,941, filed on Dec. 13, 2005; and also claims the benefit pursuant to 35 U.S.C. §119(e) of U.S. Provisional Application No. 61/167,286, filed on Apr. 7, 2009, each of which is hereby incorporated by reference in its entirety herein.

STATEMENT REGARDING FEDERALLY SPONSORED RESEARCH OR DEVELOPMENT

This invention was supported in part by funds obtained from the U.S. Government (National Institutes of Health Director's Pioneer Award number DP1-OD-04117), and the U.S. Government therefore has certain rights in the invention.

BACKGROUND OF THE INVENTION

Cellular phenotype is the conglomerate of multiple cellular processes involving gene and protein expression that result in the elaboration of a cell's particular morphology and function. It has been thought that differentiated post-mitotic cells have their genomes hard wired with little ability for phenotypic plasticity. Emerging evidence has, however, demonstrated the reversibility and flexibility of the cellular phenotype. It has been shown that fertile adult male and female frogs can be obtained by injecting endoderm nuclei into enucleated eggs (Gurdon J B, Elsdale T R, & Fischberg M (1958) sexually mature individuals of *Xenopus laevis* from the transplantation of single somatic nuclei. Nature 182:64-65). This result not only forms the foundation of the field in nuclear transplantation, but also provides evidence that the cytoplasmic components of a differentiated cell can support nuclear reprogramming. Generation of induced pluripotent stem (iPS) cells by transfection transcription factors into dividing fibroblasts (Takahashi K & Yamanaka S (2006) Induction of pluripotent stem cells from mouse embryonic and adult fibroblast cultures by defined factors. Cell 126:663-676), followed by cell selection represent a new strategy to globally revert a mature cell into a different cell type. See: Huangfu D, et al. (2008) Induction of pluripotent stem cells from primary human fibroblasts with only Oct4 and Sox2. Nat Biotechnol 26:1269-1275; Kim J B, et al. (2008) Pluripotent stem cells induced from adult neural stem cells by reprogramming with two factors. Nature 454:646-650; Nakagawa M, et al. (2008) Generation of induced pluripotent stem cells without Myc from mouse and human fibroblasts. Nat Biotechnol 26:101-106; Maherali N, et al. (2007) Directly reprogrammed fibroblasts show global epigenetic remodeling and widespread tissue contribution. Cell Stem Cell 1:55-70; Okita K, Ichisaka T, & Yamanaka S (2007) Generation of germline-competent induced pluripotent stem cells. Nature 448:313-317; and Stadtfeld M, Nagaya M, Utikal J, Weir G, & Hochedlinger K (2008) Induced Pluripotent Stem Cells Generated Without Viral Integration. Science 322:945-949. The need for re-differentiation of these ES-like-iPS cells into desired cell types, however, adds a layer of complexity that is difficult to control (Wernig M, et al. (2008) Neurons derived from reprogrammed fibroblasts functionally integrate into the fetal brain and improve symptoms of rats with Parkinson's disease. Proc Natl Acad Sci USA 105:5856-5861; Hanna J, et al. (2007) Treatment of sickle cell anemia mouse model with iPS cells generated from autologous skin. Science 318:1920-1923). Nevertheless, studies of nuclear reprogramming from genomic and epigenetic modification, as seen from somatic-cell-nuclear-transfer-cloned animals and iPS cells, suggests the flexibility of a differentiated phenotype as well as the dynamic changes of a genome (Maherali N, et al. (2007) Directly reprogrammed fibroblasts show global epigenetic remodeling and widespread tissue contribution. Cell Stem Cell 1:55-70).

Cardiomyocytes are one of the most sought after cells in regenerative medicine because of their role in repairing injured heart by replacing the lost tissue (Germani et al., 2007, Trends Mol Med 13(3): 125-33). Functional cardiomyocyte-like cells have been generated from embryonic stem cell, induced pluripotent stem (iPS) cell and direct conversion of fibroblast using defined transcription factor transduction (Takeuchi et al., 2009, Nature 459(7247): 708-11; Boheler et al., 2002, Circ Res 91(3): 189-201; Zhang et al., 2009, Circ Res 104(4): e30-41; Ieda et al., 2010, Cell 142(3): 375-86). However, carcinogenesis and early senescence often develop in transcription factors induced cells (Knoepfler, 2009, Stem Cells 27(5): 1050-6; Feng et al., 2010, Stem Cells 28(4): 704-12). It has been shown previously that transfer of the transcriptome (TIPeR) from rat astrocyte into rat neuron converted the neuron into an astrocyte-like cell (Sul et al., 2009, Proc Natl Acad Sci USA 106(18): 7624-9).

Despite the development and refinement of the techniques discussed above, there remains a need in the art for methods and compositions for effecting phenotypic change in a cell. This invention addresses that need.

BRIEF SUMMARY OF THE INVENTION

The present invention encompasses a method of effecting phenotype conversion in a cell. The method comprises introducing a second cell, the recipient cell, having a particular phenotype with phenotype-converting nucleic acid from a first cell, the donor cell, having a particular phenotype, wherein the phenotype of the first cell is different from that of the second cell. In one embodiment, the nucleic acid is introduced to the second cell by transfection. In some embodiments, the first cell is pre-treated with a transcription inhibitor. In some embodiments, the second cell is pre-treated with a transcription inhibitor before it is transfected. In some embodiments, the phenotype of the first cell differs from the phenotype of the second cell by one or more of: species, tissue type, differentiation degree, disease state, exposure to a toxin, exposure to a pathogen, and exposure to a candidate therapeutic. Optionally, the method further comprises transfecting the second cell at least a second time with the first cell mRNA transcriptome.

In one embodiment, the first cell is a cardiomyocyte. In some embodiments, the second cell is a fibroblast. Preferably, the phenotype-converting nucleic acid is the transcriptome and more preferably the mRNA transcriptome of the first cell. In one embodiment, the mRNA transcriptome comprises mRNA transcripts having an average size between about 1 kb to about 5 kb.

In some embodiments, the phenotype-converting nucleic acid further comprises one or more exogenous nucleic acids selected from the group consisting of mRNA, siRNA, miRNA, hnRNA, tRNA, non-coding RNA and combinations thereof.

In some embodiments, the cell is selected from the group consisting of a eukaryotic cell and a prokaryotic cell. The eukaryotic cell can be a non-mammalian cell or it can be a mammalian cell. In some embodiments, the eukaryotic cell is a human cell.

In some embodiments, phenotype conversion comprises a change in one or more of gene expression, protein expression, immunological markers, morphology, physiology, synthesis of bioproducts, and membrane lipid composition. In some embodiments, phenotype conversion comprises a change in expression of at least 100 genes. Phenotype conversion can comprise up-regulation of genes associated with chromosomal remodeling. In some embodiments, at least about 5% of differentially expressed genes in the second cell change expression to a level observed for the first cell.

In some embodiments, phenotype conversion persists for at least 2 weeks. In other embodiments, phenotype conversion persists for the lifetime of the cell.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 3, comprising

FIG. 4, comprising

FIG. 5, comprising

Figure 1:
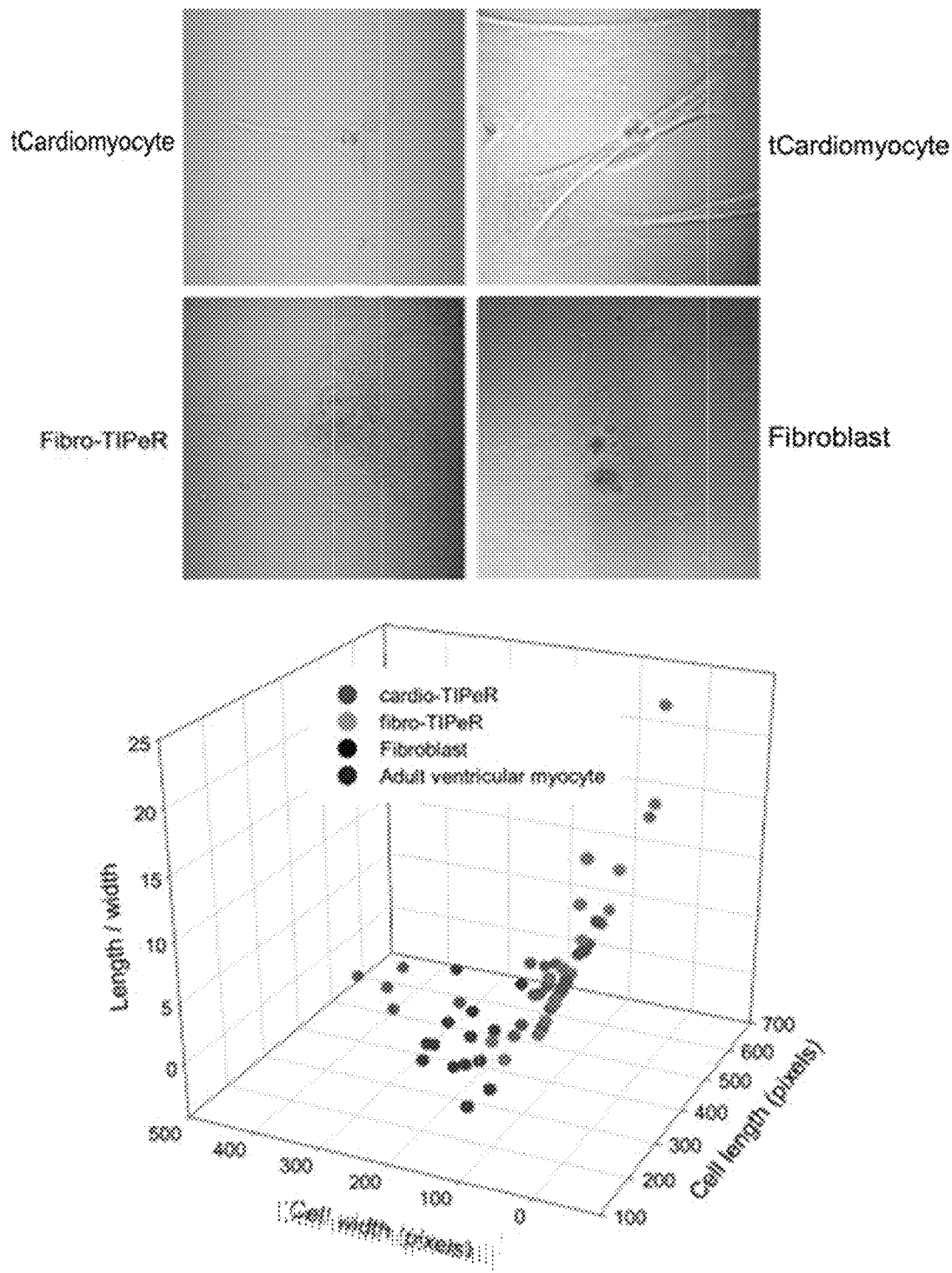
FIG. 1 depicts the results of experiments showing that tCardiomyocytes display cardiomyocyte-like morphology. (Top, photomicrographs) Live tCardiomyocyte cells display triangular or elongated morphologies (Upper), but fibro-TIPeR cells have an enlarged flat shape similar to fibroblast cells (Lower). (Bottom graph) The cell length-to-width ratio of cardio-TIPeR cells shows that the subpopulation of cardio-TIPeR cells differs from fibroblast and fibro-TIPeR cells but is similar to adult ventricular myocytes.

DETAILED DESCRIPTION OF THE INVENTION cDNA microarray analysis has shown that phenotypic differences at the cellular level are associated with differences in the presence, absence and abundances of particular RNAs. The invention described herein arises from the discovery that the relative abundances of RNAs within a population themselves can elaborate cellular phenotype. Specifically, the invention provides a method of effecting a phenotype conversion in recipient cell by introducing phenotype-converting nucleic acid from a donor cell into the recipient cell. In a preferred embodiment, the phenotype-converting nucleic acid is the mRNA transcriptome of the donor cell. The discovery described herein indicates that the plasticity of the non-dividing genome is much greater than previously imagined.

Phenotype-converting nucleic acid may include, without limitation, mRNA, siRNA, microRNA, tRNA, hnRNA, total RNA, DNA, and combinations thereof, such that the introduction of these nucleic acids into a cell and the subsequent expression of these nucleic acids results in a combined phenotype due to the multiple expression of these nucleic acids and their interactions with each other. Unlike expression systems known in the art, where one or only a few nucleic acids are expressed, the methods of the present invention permit the expression of multiple nucleic acids essentially simultaneously, resulting in an expression system closely mirroring the interaction of various nucleic acids and their expression products in a natural environment. Thus, the present invention permits the introduction of a complex mixture of nucleic acids into a cell to produce a multigenic effect, thereby effecting phenotype conversion of a cell.

The methods of the present invention are performed by transfecting a mixture of nucleic acids into live cells. The methods of the invention utilize a wide variety of methods of transfection, including those known in the art and those described herein.

The present invention permits the transfection of nucleic acid, preferably mRNA and/or DNA into a cell with accurate control of the amount of nucleic acid entering the cell, thus allowing the skilled artisan to mimic the expression level of nucleic acid in a cell under desired conditions, as disclosed elsewhere herein. That is, the present invention allows the skilled artisan to accurately control the level of nucleic acid transfected into a cell by modulating the concentration of nucleic acid in the extracellular environment of the cell.

In one embodiment, the present invention includes methods for phenotype conversion of a cell using laser-aided poration of live cell membranes coupled with bath application of nucleic acids, preferably a transcriptome, in order to transfect a mixture of nucleic acids into a live cell. Photoporation is advantageous in enabling highly location-specific transfection of a cell and permitting multiple poration events, while not detrimental to cellular function or viability. Further, the precise amount of nucleic acid transfected into a cell can be modulated through regulation of laser intensity, pore size and number, and duration of membrane opening, as well as repetition of transfection.

The methods of the present invention are not limited to cells, but can further include live slices of tissue and live animals, preferably mammals, as disclosed elsewhere herein. The methods of the present invention can further comprise other non-mammalian cells eukaryotic cells and prokaryotic cells, such as bacterial cells, yeast cells, plant cells, protozoa, insect cells, fungal cells, including filamentous and non-filamentous fungi, and the like.

DEFINITIONS

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein, "phenotype conversion" refers to the induction or establishment of a destination phenotype. Phenotype conversion comprises a change in at least one of gene expression, protein expression, immunological markers, morphology, physiology, synthesis of bioproducts (e.g., dopamine) and membrane lipid composition.

As used herein, a "destination phenotype" refers to a phenotype of interest that is induced in a recipient cell by the introduction therein of a mixture of nucleic acids. The phenotype of interest may be any phenotype. For example, a destination phenotype may be a morphological change. A destination phenotype may be a physiological change, such as the presence of voltage-gated calcium receptors in a recipient cell. A destination phenotype may comprise more than one phenotypic change and may even cause the cell to assume characteristics of a different tissue type from its original tissue type.

The phrase "phenotype-converting nucleic acid" refers herein to a mixture of nucleic acid that is capable of establishing a destination phenotype in a recipient cell. Phenotype-converting nucleic acid is not limited to the empirical content of RNA in a donor cell, but rather, encompasses the relative abundance of each RNA with respect to each in a population of RNAs such that the population of RNAs are necessary and sufficient to induce a destination phenotype in a recipient cell.

As used herein, "transcriptome" refers to the collection of all gene transcripts in a given cell and comprises both coding RNA (mRNAs) and non-coding RNAs (e.g., siRNA, miRNA, hnRNA, tRNA, etc.). As used herein, an "mRNA transcriptome" refers to the population of all mRNA molecules present (in the appropriate relative abundances) in a given cell. An mRNA transcriptome comprises the transcripts that encode the proteins necessary to generate and maintain the phenotype of the cell. As used herein, an mRNA transcriptome may or may not further comprise mRNA molecules that encode proteins for general cell existence, e.g., housekeeping genes and the like.

As used herein, "TIPeR" refers to the process of transfecting a recipient cell with a transcriptome from a donor cell. A cell that has undergone this process may be referred to herein as a TIPeRed cell.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A "fluid medium" or "fluid media" is used herein to refer to a form of matter, such as air, liquid, solid or plasma, preferably liquid, that is capable of flowing.

An "isolated cell" refers to a cell which has been separated from other components and/or cells which naturally accompany the isolated cell in a tissue or mammal.

As applied to a protein, a "fragment" of a polypeptide, protein or an antigen, is about 6 amino acids in length. More preferably, the fragment of a protein is about 8 amino acids, even more preferably, at least about 10, yet more preferably, at least about 15, even more preferably, at least about 20, yet more preferably, at least about 30, even more preferably, about 40, and more preferably, at least about 50, more preferably, at least about 60, yet more preferably, at least about 70, even more preferably, at least about 80, and more preferably, at least about 100 amino acids in length amino acids in length, and any and all integers there between.

A "genomic DNA" is a DNA strand which has a nucleotide sequence homologous with a gene as it exists in the natural host. By way of example, a fragment of a chromosome is a genomic DNA.

As used herein, an "inhibitory nucleic acid" refers to an siRNA, a microRNA, an antisense nucleic acid or a ribozyme.

As used herein, "locally transfecting" a nucleic acid refers to introducing a nucleic acid into a region of cytoplasm that is not the entirety of the cytoplasm of a cell optionally comprising a cellular process.

As used herein, "porate" or "porates" refers to creating a hole in a surface through which compounds can pass.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are completely or 100% homologous at that position. The percent homology between two sequences is a direct function of the number of matching or homologous positions, e.g., if half (e.g., five positions in a polymer ten subunits in length) of the positions in two compound sequences are homologous then the two sequences are 50% identical, if 90% of the positions, e.g., 9 of 10, are matched or homologous, the two sequences share 90% homology. By way of example, the DNA sequences 5'ATTGCC3' and 5'TATGGC3' share 50% homology.

In addition, when the terms "homology" or "identity" are used herein to refer to the nucleic acids and proteins, it should be construed to be applied to homology or identity at both the nucleic acid and the amino acid sequence levels.

The term "multigenic phenotype" is used herein to refer to a phenotype in a cell, tissue or animal that is mediated by the expression or lack of expression of two or more nucleic acids encoding a protein, wherein the nucleic acids are exogenously provided to the cell, tissue or animal.

"Recombinant polynucleotide" refers to a polynucleotide having sequences that are not naturally joined together. An amplified or assembled recombinant polynucleotide may be included in a suitable vector, and the vector can be used to transform a suitable host cell.

A recombinant polynucleotide may serve a non-coding function (e.g., promoter, origin of replication, ribosome-binding site, etc.) as well.

A host cell that comprises a recombinant polynucleotide is referred to as a "recombinant host cell." A gene which is expressed in a recombinant host cell wherein the gene comprises a recombinant polynucleotide, produces a "recombinant polypeptide."

A "recombinant polypeptide" is one which is produced upon expression of a recombinant polynucleotide.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Phototransfection" is used herein to refer to a process by which a hole is created in a barrier, such as a cell membrane, using a photon source, such as a laser, and two or more nucleic acids, wherein the nucleic acids encode different polypeptides, are inserted into a cell through the hole in the cell membrane.

By "tag" polypeptide is meant any protein which, when linked by a peptide bond to a protein of interest, may be used to localize the protein, to purify it from a cell extract, to immobilize it for use in binding assays, or to otherwise study its biological properties and/or function.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention provides methods of introducing mixtures of nucleic acids into a recipient cell to produce a phenotype-conversion in the recipient cell. The present invention comprises transfecting phenotype-converting nucleic acid, preferably RNA and/or DNA, even more preferably mRNA, and most preferably, an mRNA transcriptome, locally into a recipient cell. The phenotype of the donor cell is different from the phenotype of the recipient cell. The difference in phenotype may be any difference, such a difference in species, tissue type, extent of differentiation, exposure to a drug or pathogen, disease state, growth conditions and so forth, wherein the difference is known or suspected of resulting from a difference in gene expression.

As shown herein, transfection with an mRNA transcriptome yields a high degree of phenotype conversion. Where multiple cells are transfected in accordance with the method of the invention, at least about 25% of the cells undergo phenotype conversion. In some embodiments, phenotype conversion in at least about 35% of recipient cells is observed.

The recipient cell may be any type of cell. A recipient cell may be a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell, the cell is a bacterial cell. A recipient cell may be a differentiated cell and/or a non-dividing cell. The cell may also be a progenitor cell or a stem cell. Preferably, the recipient cell is a tissue-specific cell, more preferably a mammalian tissue-specific cell and more preferably still, a human tissue-specific cell. Non-limiting examples of cells suitable as recipient cells include epithelial cells, neurons, fibroblasts, embryonic fibroblasts, keratinocytes, adult stem cells, embryonic stem cells, and cardiomyocytes.

To obtain the desired phenotype conversion, recipient cells are preferably phenotypically-pliable cells. Phenotypically-pliable cells are cells whose phenotype is amenable to changing under the conditions of the method of the invention. Non-limiting examples of phenotypically-pliable cells include neurons, fibroblasts, embryonic fibroblasts, adult stem cells and embryonic stem cells. Preferably, the cell is a fibroblast, and the nucleic acid is RNA, even more preferably, mRNA and more preferably still, an mRNA transcriptome.

In the method of the invention, nucleic acid is transferred into a cell to initiate phenotype conversion in the recipient cell. As used herein, phenotype conversion comprises a change in at least one of gene expression, protein expression, immunological markers, morphology, physiology, synthesis of bioproducts (e.g., dopamine) and membrane lipid composition. Preferably, the change yields a phenotype associated with or indicative of the cell from which the transfected RNA or DNA is obtained. Preferably, phenotype conversion in the recipient cell comprises two or more changes. More preferably, phenotype conversion comprises three or more changes. In one embodiment, phenotype conversion comprises a change in physiology. In another embodiment, phenotype conversion comprises a change in morphology and a change in physiology of the recipient cell. Phenotype conversion may be accompanied by changes in expression in hundreds of genes. For instance, expression of genes quiescent in both the donor and the recipient cells may be de novo up-regulated. Genes associated with chromosomal remodeling, such as genes involved in chromosome and DNA metabolism related process, may be up-regulated in cells having phenotype conversion. Genes annotated "BP" in the Gene Ontology ("GO") database are considered associated with chromosomal remodeling (The Gene Ontology Consortium (2000) "Gene ontology: tool for the unification of biology," Nature Genet. 25:25-29). The GO database is publicly available (see www.geneontology.org). In some embodiments, at least about 5%, more preferably about 7%, 10%, 15% and more preferably still at least about 25% of genes that are expressed differently in the recipient cell compared to the donor cell (e.g., differentially expressed genes) based on gene expression profiling have their expression changed to the level observed for the donor cell.

Phenotype conversion in the recipient cell is maintained stably for extended periods of time. In one embodiment, phenotype conversion is stable and persists for at least about 1 day, 2 days, 3 days, 4 days, 5 days, 6 days, 7 days, 8 days, 9 days, 10 days, 11 days, 12 days, 13 days, or more. In one embodiment, phenotype conversion is stable for at least about 1 week, 2 weeks, 3 weeks, 4 weeks, or more. In another embodiment, phenotype conversion is stable for at least about 1 month, 2 month, 3 months or more. In preferred embodiments, phenotype conversion is stable for the duration of the recipient cell's lifespan or the lifespan of a culture derived from the recipient cell.

Phenotype-converting nucleic acid may comprise two or more nucleic acids having different sequences. In some embodiments, the two or more nucleic acids encode different polypeptides. In other embodiments, the nucleic acids are non-coding RNAs or other non-coding nucleic acids. In yet other embodiments, the nucleic acids comprise a mixture of coding and non-coding nucleic acids. In preferred embodiments, the phenotype-converting nucleic acid comprises the transcriptome, preferably the mRNA transcriptome, from a donor cell. In other embodiments, the phenotype-converting nucleic consists only of the transcriptome or mRNA transcriptome from a donor cell. Nucleic acids may be obtained from a donor cell or may be chemically synthesized or a combination thereof. Methods for chemically synthesizing a nucleic acid are disclosed elsewhere herein and can include in vitro transcription.

An mRNA transcriptome may comprise mRNAs encoding 3 or more, 5 or more, 10 or more, 20 or more, 40 or more, 50 or more, 75 or more, 100 or more, 200 or more different polypeptides.

The method of the invention may be carried on a cell comprising a cellular process. Such a cellular process includes, but is not limited to, an electrical property such as an action potential, a dendrite, an axon, a microvilli, a cilia, a stereocilia, a process, an astrocytic process, and the like. As demonstrated herein, this method advantageously permits the introduction of a desired amount of nucleic acid into one or more local sites, permitting the controlled and localized production of protein in physiological amounts, resulting in a multigenic effect in a cell. This method thus allows specific localization of exogenously applied nucleic acid, preferably mRNA, without resorting to severing the cellular process from the cell to which it is attached (Kacharmina, et al., 2000, Proc. Nat'l Acad. Sci. USA, 97:11545-11550). Further, the present method permits the expression of an mRNA transcriptome of a donor cell, thus resulting in phenotype conversion in the recipient cell.

The present invention further comprises methods for transfecting a live slice of tissue or a live animal. Methods for sustaining the cellular processes in the cells comprising a live slice of tissue are known in the art. As a non-limiting example, live slices can be refrigerated and perfused with natural or artificial fluids, such as artificial spinal fluid, artificial central nervous system fluid, and buffers disclosed elsewhere herein. Methods for the manipulation of live slice cultures are described in, for example, Roelandse, et al. (2004, J. Neuroscience, 24: 7843-7847); and Chen, et al. (2005, Magn. Reson. Med. 53: 69-75).

Methods for transfecting a live animal, preferably a mammal, are performed using the methods described herein combined with methods of animal and human surgery known in the art. Exemplary surgical procedures contemplated for use with the methods of the invention include cardiac catherization, angioplasty, arthroscopy, laparoscopy, tumor resection, surgical placement of a therapeutic implant and the like. Mammals contemplated in the present invention include, but are not limited to, mice, rabbits, rats, goats, guinea pigs, humans, and the like.

As a non-limiting example, one or more nucleic acids is applied to a tissue in a live animal to transfect the tissue in the live animal with one or more nucleic acids. The nucleic acid is introduced to the animal using methods disclosed elsewhere herein, such as through a microscope or an optical fiber or endoscopy. The expression of a polypeptide transfected using the methods of the present invention is monitored using methods of detecting protein expression known in the art, such as Western blots, immunocytochemistry, in situ protein detection, and the like. Methods for using a laser to manipulate animal tissues are well known in the art and are described in, for example, Dang, et al. (2005, Exp Dermatol., 14: 876-882).

The methods disclosed herein comprise introducing phenotype-converting nucleic acid, preferably RNA and more preferably mRNA, siRNA, miRNA, hnRNA, tRNA, non-coding RNAs and combinations thereof, including but not limited to total mRNA, to a cell and transfecting the cell at one or more sites on the cell membrane. Preferably, the phenotype-converting nucleic acid introduced into a cell is an mRNA transcriptome. The cell is preferably a primary cell culture or in slice culture. The cell can be transfected at any site. The nucleic acid can be provided to the cell by any method known to the skilled artisan, and is preferably provided by means of a nucleic acid bath comprising a mixture of nucleic acids, disclosed elsewhere herein. A nucleic acid bath is a solution comprising a nucleic acid of interest in which a cell is bathed. In one embodiment, bath application of the cell comprises surrounding the cell with a solution comprising nucleic acid, thus bathing the entire cell. In one embodiment, the cell is then irradiated with a laser at one or more sites located anywhere on the cell. In another embodiment, bath application comprises bathing a discrete portion or portions of a live cell, for instance, by applying a solution comprising nucleic acid to a discrete location on the surface of the cell. In one embodiment, the cell is then irradiated one or more times within the discrete location or locations that was bathed. The discrete location bath is advantageous because it creates a greater mRNA concentration gradient, which allows mRNAs to diffuse more efficiently through the temporary poration holes into the porated cell. It also requires less mRNAs (e.g., 0.3 µg) than the bath application (e.g., 20 µg). In either case, the solution is appropriately buffered and is of the proper pH to maintain the structural integrity of the cell to be transfected.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a cell include calcium phosphate precipitation, lipofection, particle bombardment, microinjection, electroporation, phototransfection and the like. Methods for producing cells comprising vectors and/or exogenous nucleic acids are well-known in the art. See, for example, Sambrook et al., MOLECULAR CLONING: A LABORATORY MANUAL volumes 1-3 (3rd ed., Cold Spring Harbor Press, N Y 2001).

Biological methods for introducing a polynucleotide of interest into a cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome {e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −200 C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Phenotype-converting nucleic acid suitable for use in the method of the invention may be of any size. For instance, a nucleic acid of about 800 nucleotides and a nucleic acid of about 3000 nucleotides have been successfully transfected into cells. However, the methods of the present invention are not limited to a nucleic acid, preferably an RNA, of the sizes disclosed herein. The present invention comprises transfecting a nucleic acid of about 30 bases, even more preferably, about 50 bases, yet more preferably, about 75 bases, even more preferably, about 100 bases, yet more preferably, about 75 bases, even more preferably, about 100 bases, yet more preferably, about 150 bases, even more preferably, about 200 bases, yet more preferably, about 300 bases, even more preferably, about 500 bases, yet more preferably, about 750 bases, even more preferably, about 1000 bases, yet more preferably, about 1500 bases, even more preferably, about 2000 bases, yet more preferably, about 2500 bases, even more preferably, about 3000 bases, in length. Even more preferably, the present invention comprises transfecting, sometimes by phototransfection, a mixture of RNAs encoding different proteins and of different molecular weights. In preferred embodiments, the phenotype-type converting nucleic acid is an mRNA transcriptome having a range of mRNA transcript sizes and having an average mRNA transcript size from about 0.5 kb to about 5 kb, more preferably, from about 1 kb to about 3.5 kb. As a non-limiting example, the mRNA transcriptome is obtained from cardiomyocyte, wherein the average size of the mRNA transcriptome is about. In some embodiments, the transcriptome is transfected into a recipient cell, such as a fibroblast, to induce phenotype conversion of the fibroblast to the tCardiomyocyte phenotype. In other embodiments, the transcriptome is transfected into a recipient cell, such as a fibroblast, to induce phenotype conversion of the fibroblast to the induced pluripotent stem (iPS) cell phenotype.

As another non-limiting example, a nucleic acid expression profile of a cell in a desired physiological state (e.g. during differentiation, in a disease state, after treatment with a pharmaceutical, toxin, transcription inhibitor, or other compound) and a nucleic acid expression profile of a cell in another physiological state (e.g. the same cell type pre- or post-differentiation, not in a disease state, or before treatment with a pharmaceutical, toxin, transcription inhibitor or other compound) can be obtained using techniques for RNA isolation known in the art and disclosed elsewhere herein. The cDNA clones of these RNAs can be generated, reflecting the altered RNA abundances of the differing physiological states, or the RNA can be transfected into a cell without first reverse transcribing the RNA to cDNA. These RNA can be mixed according to the same ratios and abundances indicated by the nucleic acid expression profiles of the cells in differing physiological states. These nucleic acid mixtures are then transfected into a cell using the transfection methods disclosed herein, and those known in the art. The methods of the present invention permit the local transfection of a cell, and therefore the nucleic acid mixture can be locally transfected to a specific part of a cell, or the nucleic acid mixture can be generally transfected into a cell by transfecting any portion of the cell. Using the methods of the present invention, and the physiologically relevant mixtures of nucleic acids described herein, once the mixture of nucleic acids is expressed in a cell, the phenotype of the physiological state can be replicated in a cell or a cellular process, thus allowing the skilled artisan to observe the phenotype transfer in a cell or cellular process.

Nucleic acid, preferably a transcriptome, may be obtained from any cell of interest in any physiological state, such as, for example, a cardiomyocyte. The donor cell may be any type of cell. A donor cell may be a eukaryotic cell or a prokaryotic cell. When the cell is a eukaryotic cell, the cell is preferably a mammalian cell, including but not limited to human, non-human primate, mouse, rabbit, rat, goat, guinea pig, horse cell, and the like. A non-mammalian eukaryotic cell includes a yeast cell, a plant cell, an insect cell, a protozoan cell and a fungal cell, including filamentous and non-filamentous fungi. When the cell is a prokaryotic cell the cell is a bacterial cell. Non-limiting examples of cells from which nucleic acid may be obtained include astrocytes, cardiomyocytes, neonatal cardiomyocytes, embryonic stem cells and neurons. RNA from any donor cell of interest can be transfected into any recipient cell in the method of the invention, such as, for example, a fibroblast. Preferably, donor cells are of the same species as the recipient cells. Donor cells may be from the same individual as the recipient cell, or from a different individual. Donor cells may originate from the same germinal layer (e.g., ectoderm) as the recipient cell (e.g. both arise from ectoderm germ layer), or from a different germinal layer (e.g., one cell arises from ectoderm and the other arises from endoderm germ layer). Donor cells may be the same cell type as the recipient cell but at a different stage of differentiation, exposed to a candidate therapeutic, exposed to a toxin or pathogen, diseased. In yet other embodiments, a donor cell may be a recipient cell. For instance, nucleic acid from a donor cell is transferred into a first recipient cell. Nucleic acid from the first recipient cell is then subsequently transferred into a second recipient cell. In one aspect, the first and second recipient cells are in different physiological states. In another aspect, the first and second recipient cells are the same type of cell. As described elsewhere herein, RNA obtained from a cell may be used to transfect a cell, or may be used as a template to create cDNA. The cDNA may be used in in vitro transcription methods to amplify some or all of the RNA, which is then used in the method of the invention.

As a non-limiting example, the total RNA from a cardiomyocyte or other progenitor cardiomyocyte cell can be isolated from such a cell using techniques known in the art and disclosed elsewhere herein. To obtain an mRNA transcriptome, the total RNA can then be processed using various methods known in the art for isolating mRNA, such as isolation of mRNA using complementary poly-dT nucleic acids, which can be conjugated to beads or a column. The total mRNA obtained is then transfected into a recipient cell using the methods disclosed herein. The recipient cell then expresses the mixture of mRNA isolated from the cardiomyocyte and replicates the multigenic effect of the differential gene translation and regulation characteristic of a developing cardiomyocyte. The present invention is not limited to cardiomyocytes or their progenitors however, and can be used to determine the transferred multigenic phenotype of any type of developing or developed cell, provided that the total RNA and mRNA are isolated from the cell.

As non-limiting example, the total RNA from a cell treated with a compound, such as a drug, a peptide, a cytokine, an antibody, a mitogen, a toxin, a transcription inhibitor or other compounds known in the art, can be isolated using the methods disclosed herein and known in the art. The mRNA from that cell can then be transfected into another cell type using the methods disclosed herein, thus transferring the multigenic phenotype of the cell treated with a compound to another cell, thus enabling the rapid and specific determination of that compound on another cell type.

In another non-limiting embodiment of the present invention, the total RNA from a diseased cell, such as a tumor cell, a cell harboring an intracellular pathogen, a cell from a patient with an autoimmune disease, and the like, can be isolated from the diseased cell. The mRNA transcriptome from that cell can be isolated from the total RNA using, for example, poly-dT isolation techniques. The mRNA from the diseased cell is transfected into another cell using the methods of the present invention, thus transferring the multigenic phenotype of the diseased cell to another cell, providing a more accurate picture of the role interacting nucleic acids and their encoded proteins have in the phenotype of a cell.

As another non-limiting embodiment of the invention, the method of the invention can be practiced in order to prepare cells for testing therapeutics. Candidate therapeutics are typically tested on a number of different cell types, prior to assessment in animals or humans. These different cells often are cell lines that have a multiplicity of signaling pathways. The multiplicity of pathways may overlap and compensate for drug function and testing with regard to efficacy and/or side effects, thereby making assessment of the candidate drug effects less robust. According, it is contemplated that mRNA for one or more specified second messenger system pathways can be transfected into primary cells or cell lines of interest in order to create cells having enriched presence and/or activity of one or more pathways, thus these pathways will dominate over endogenous pathways. The mRNA are therefore a heterogeneous collection of mRNAs that encode the various components for the one or more second messenger system pathways. Enriched presence and/or activity of one or more pathways is relative to a cell that has not had mRNA for one or more specified second messenger system pathways transfected into it. Candidate therapeutics can then be assessed for efficacy and/or side effects on the dominant pathways present in the cells with enriched expression of one or more specified second messenger system pathways. Non-limiting examples of second messenger systems include: the cAMP system; the phosphoinositol system; the arachidonic acid system; the cGMP system; and the tyrosine kinase system. It is expected that using such defined cell types permits improved assessment of the effect of a candidate on particular pathways. In one embodiment, modulation of endogenous pathways by decreasing expression of particular pathways is also contemplated. Modulation can be achieved by introducing siRNAs corresponding to mRNAs encoding particular proteins in a pathway into the cell to inhibit particular pathways. Such modulation can be performed simultaneously with the introduction of the mRNAs for the one or more specified second messenger system pathways, or can be done in one or more separate steps. In one embodiment, an embryonic fibroblast is used as the recipient cell. In one embodiment, the donor cells from which total RNA is obtained are cardiomyocytes and the recipient cell type is an embryonic fibroblast. In a preferred aspect, mRNA is extracted from the cardiomyocyte total RNA and is transfected into the embryonic fibroblast.

In another non-limiting embodiment, the method of the invention can be used to generate a knock out (KO) of one or more specific genes in a cell. The field of functional genomics has relied upon the generation of KO mice to elucidate the function of particular genes. The utility of KO mice has been enhanced by flanking a gene with FLOX-sites, which are recognized by CRE-recombinase. CRE-recombinase binds to FLOX-sites and removes the intervening sequence containing the gene, thereby knocking out that gene. Cell-type specific KO has been achieved by driving CRE-recombinase expression in particular cell types using cell-type specific promoters. Inducible promoters, such as TET-on or the ecdysone system, have been used to control the time of induction of CRE-recombinase expression; expression is induced upon exogenous addition of the cognate inducer. Advantageously, the method of the invention can be used to knock out a gene in a particular cell at a particular time without the use of inducible promoters and exogenous inducers. In one embodiment, mRNA encoding CRE-recombinase, or the protein itself, is transfected into cells having chromosomal material engineered genetically to contain FLOX sites flanking one or more genes of interest. The transfection can be done with a single engineered cell or with a population of the engineered cells. The method can also be practiced with live tissue samples or with a live animal. The method is not limited to the use of CRE-recombinase and FLOX sites. It can be practiced using any comparable system of specific sequence excision, such as zinc-finger nuclease technology and the FLP recombinase and FRT system. The method can also be used for targeted integration of a gene.

The present invention can further comprise the use of a nucleic acid from a cell or a population of cells of homogeneous or heterogeneous types. The present invention can further comprise the use of a nucleic acid, preferably mRNA, defined by the expression profile of a cell as determined using methods well known in the art, including, but not limited to, a gene array profile, total RNA, total mRNA, and the like. An expression profile is used to determine the relative abundances of mRNA in a cell. The expression profile is then used as a template to determine the relative abundances of mRNA in the physiological state of the cell from which the expression profile was made. A population of mRNA with the same relative abundance as in the cell for which expression has been profiled is produced using the methods disclosed elsewhere herein, including mRNA isolation, in vitro transcription or chemical synthesis. The resultant population of mRNA is then transfected into the cell using the methods described elsewhere herein, thereby transferring the phenotype of the cell from which the expression profile was made to another cell, tissue or animal.

In another embodiment, a population of mRNA reflecting the relative abundance of a cell in a particular physiological state further comprises mRNA encoding one or more polypeptides that facilitate phenotype conversion. For instance, the mRNA obtained from a neuronal cell may be supplemented with mRNA encoding proteins that stimulate exocytosis and is then transfected into a non-neuronal recipient cell.

The present invention may further comprise the sequential transfection of a cell. Sequential transfection is used herein to refer to a process in which a cell is transfected at a first time point, and then transfected at a second or subsequent time point. As an example, a cell can be transfected on day 1, the result of which is that one or more nucleic acids are introduced into the cell. These nucleic acids can be expressed by the cellular translation complexes or remain silent, or can be inhibited using an inhibitory nucleic acid as disclosed elsewhere herein. On day 2, the same cell can be transfected again, transfecting one or more of the same or dissimilar nucleic acids to the same cell. The present invention is not limited to transfection separated by a day however. Sequential transfection can occur with minutes, hours, days, weeks or months between a first time point and a second time point, provided the transfection occurs to the same cell. Thus, the sequential transfection methods of the present invention are limited only by the lifespan of the cell. Another non-limiting example of sequential transfections comprises a first transfection on Day 1, a second transfection 48 hours later (Day 3) and a third transfection 7 days after the first transfection. The conditions of sequential transfection may be the same or different. The means of transfection may be changed and/or the number of sites transfected in a transfection step may be different among multiple transfections. For instance, the second and subsequent transfections using transfection may be performed using a reduced laser power compared to the laser power used in the first transfection.

The sequential transfection methods of the present application are useful for, among other things, analyzing temporal gene expression in a cell, analyzing the multigenic effects of a protracted developmental process, and determining the relationship of genotype to phenotype over the course of the viable life span of a cell. Sequential transfection using the same nucleic acids also increases the robustness of expression of the phototransfected nucleic acids. As shown herein, three sequential transfections of cardiomyocyte transcriptome into a fibroblast yields a durable phenotype conversion in a high percentage of fibroblast cells.

The embodiments of the inventions disclosed herein are not limited to mRNA. The present invention can further comprise reverse transcribing mRNA into cDNA, then transfecting the cDNA into a cell The present invention is not limited to the use of RNA and mRNA. A mixture of DNA and RNA can be used in the methods of the present invention to determine the effects of transient (RNA) as well as prolonged (DNA integration into the genome) gene expression in a cell.

When a mixture of nucleic acids, such as a mixture of RNAs is transfected into a cell, subpopulations of that mixture can be transfected into a cell to determine the core set of RNAs responsible for a given phenotype. As a non-limiting example, when the total RNA is isolated from a cell in a certain physiological state and mRNA is isolated from that population of total RNA, specific subpopulations of the isolated mRNA can be transfected into a cell to establish the core mRNAs responsible for that phenotype. The present embodiment can also be performed with cDNA produced from mRNA. Specific populations of mRNA can be identified using sequence homology data or other characteristic features known in the art and available from various databases, such as GenBank® (United States Department of Health and Human Services, Bethesda Md.).

Alternatively, the mRNA from a cell can be isolated and transfected into a cell using the methods of the present invention, and an siRNA, microRNA, antisense nucleic acid or ribozyme (collectively referred to as an inhibitory nucleic acid) can be transfected along with the mRNA, resulting in silencing and/or inhibition of an mRNA. Silencing an mRNA permits one of skill in the art to identify, for instance, the core mRNA(s) responsible for a multigenic phenotype. In addition, the present invention allows the replication of a phenotype in another cell without the step of determining the nucleic acid expression profile of a cell in a physiological state. The nucleic acid, preferably RNA, from a cell in a specific physiological state, such as a certain differential or disease state, can be isolated. Preferably, an mRNA transcriptome is then isolated. Using the methods of the present invention, the RNA, or a cDNA of the RNA, can be transfected into a cell in order to analyze the phenotype in the transfected cell once the nucleic acid has been expressed. The nucleic acid, preferably RNA, can be the total RNA from a cell, or a subpopulation of the RNA, such as the mRNA transcriptome.

To assess the effect of expression of the transfected nucleic acids, cells transfected in accordance with the method of the invention can be examined using methods known in the art. Assessments may be made, for example, of phenotypic changes, mRNA expression, protein expression and functional assays. Examples of such analyses include, but are not limited to, cell morphology, presence and absence of immunological markers, RT-PCR, expression profiling, mRNA abundance measurements, immunocytochemistry analysis (ICC) for specific proteins, cell viability, and cell-specific activities, such as cell division-mitosis and electrophysiology.

Optionally, the present method further comprises inhibiting transcription in the transfected cell, thus preventing competition between expression of endogenous and exogenous mRNAs and the proteins encoded thereby. Transcription can be inhibited by addition of exogenous agents, such as an inhibitory nucleic acid or compounds that inhibit transcription, such as 5,6-Dichloro-1-β-D-ribofuranosylbenzimidazole (DRB), a protease, or SP100030 (Huang et al., 2001, Br. J. Pharmacol., 134: 1029-1036). Other agents useful for inhibiting transcription in a recipient cell include, but are not limited to, α-amanitin, trichostatin A (TSA; a histone deacetylase inhibitor), tubulin depolymerizer and actin depolymerizer. Preferably, a recipient cell is contacted with one or more transcription inhibition agents prior to transfection. Preferably, the cell is contacted between about 30 minutes and about 80 hours, preferably between about 30 minutes and about 60 hours and more preferably, between about 6 hours to about 48 hours, prior to transfection.

The present method can also be used for the specific and local transfection of an inhibitory nucleic acid, such as an siRNA, antisense nucleic acid or a microRNA (miRNA), using the methods of the present invention. Using the invention disclosed herein, the skilled artisan can specifically inhibit a cellular nuclear acid, especially those in cellular processes. Further, as disclosed elsewhere herein, an inhibitory nucleic acid can be used to identify the core nucleic acid(s) involved in a multigenic phenotype.

The phenotype-converting nucleic acids useful in the methods of the present invention may comprise a variety of nucleic acids, including various species of RNA (mRNA, siRNA, miRNA, hnRNA, tRNA, total RNA, combinations thereof and the like) as well as DNA. Methods for isolating RNA from a cell, synthesizing a short polynucleotide, constructing a vector comprising a DNA insert, and other methods of obtaining a nucleic acid to phototransfect into a cell are well known in the art and include, for example, RNA isolation, cDNA synthesis, in vitro transcription, and the like.

The nucleic acid compositions of this invention, whether RNA, cDNA, genomic DNA, or a hybrid of the various combinations, may be isolated from natural sources or may be synthesized in vitro. Techniques for nucleic acid manipulation are described generally in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York)., incorporated herein by reference. Nucleic acids suitable for use in the present method also include nucleic acid analogs. Examples of such analogs include, but are not limited to, phosphorothioate, phosphotriester, methyl phosphonate, short chain alkyl or cycloalkyl intersugar linkages, or short chain heteroatomic or heterocyclic intersugar ("backbone") linkages. In addition, nucleic acids having morpholino backbone structures (U.S. Pat. No. 5,034,506) or polyamide backbone structures (Nielsen et al., 1991, Science 254: 1497) may also be used.

The methods of the present invention can comprise the use of a variety of nucleic acids, including DNA, RNA, a cDNA reverse transcribed from an mRNA, an RNA transcribed from that cDNA, a DNA amplified from the cDNA, an RNA transcribed from the amplified DNA, and the like. The present invention further comprises using single-stranded and double-stranded RNA and DNA molecules. Any coding sequence of interest can be used in the methods of introducing and translating a nucleic acid in a cell or in a cellular process, such as a dendrite. One of skill in the art will understand, when armed with the present disclosure, that a multitude of properties of a cellular process, and by association, of the attached cell, can be affected by the methods of the present invention.

In one embodiment of the present invention, the nucleic acid transfected into a cell is all or a portion of the total mRNA isolated from a biological sample. The term "biological sample," as used herein, refers to a sample obtained from an organism or from components (e.g., organs, tissues or cells) of an organism. The sample may be of any biological tissue or fluid. The nucleic acid (either genomic DNA or mRNA) may be isolated from the sample according to any of a number of methods well known to those of skill in the art.

Methods of isolating total mRNA are well known to those of skill in the art. For example, methods of isolation and purification of nucleic acids are described in detail in Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993) and Chapter 3 of Laboratory Techniques in Biochemistry and Molecular Biology: Hybridization With Nucleic Acid Probes, Part I. Theory and Nucleic Acid Preparation, P. Tijssen, ed. Elsevier, N.Y. (1993)).

Preferably, the total nucleic acid is isolated from a given sample using, for example, an acid guanidinium-phenol-chloroform extraction method and polyA$^+$ mRNA is isolated by oligo dT column chromatography or by using (dT)n magnetic beads. Commercially available products, such as TRIZOL and MICRO-FASTTRACK (Invitrogen™, Carlsbad, Calif.), are useful in extracting nucleic acid from a biological sample.

The mRNA can be locally transfected directly into a cell or a cellular process, or the sample mRNA can be reverse transcribed with a reverse transcriptase and a promoter comprising an oligo dT and a sequence encoding the phage T7 promoter to provide single stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro polymerization are well known to those of skill in the art (see, e.g., Sambrook, supra.; Van Gelder, et al., 1990, Proc. Natl. Acad. Sci. USA, 87: 1663-1667). Moreover, Eberwine et al. (1992, Proc. Natl. Acad. Sci. USA, 89: 3010-3014) provide a protocol using two rounds of amplification via in vitro transcription to achieve greater than $10^6$ fold amplification of the original starting material.

The present invention further comprises the use of in vitro transcription for transfection into a cell or cellular process. In vitro transcription comprises the production of dsRNA by transcribing a nucleic acid (DNA) segment in both directions. For example, the HiScribe™ RNAi transcription kit (New England Biolabs, Ipswich, Mass.) provides a vector and a method for producing a dsRNA for a nucleic acid segment that is cloned into the vector at a position flanked on either side by a T7 promoter. Separate templates are generated for T7 transcription of the two complementary strands for the dsRNA. The templates are transcribed in vitro by addition of T7 RNA polymerase and dsRNA is produced. Similar methods using PCR and/or other RNA polymerases (e.g., T3 or SP6 polymerase) can also be used and are known in the art.

The present invention further comprises the use of chemically synthesized nucleic acids for use in transfection. Oligonucleotides for use as probes can be chemically synthesized according to the solid phase phosphoramidite triester method first described by Beaucage, (1981, Tetrahedron Letts., 22:1859-1862) using an automated synthesizer, as described in Needham-VanDevanter, et al. (1984, Nucleic Acids Res., 12:6159-6168). Purification of oligonucleotides is by either native acrylamide gel electrophoresis or by anion-exchange HPLC as described in Pearson (1983, J. Chrom., 255:137-149). The sequence of the synthetic oligonucleotides can be verified using the chemical degradation method of Maxam (1980, in Grossman and Moldave, eds., Methods in Enzymology, Academic Press, New York, 65:499-560).

The present invention can further comprise the use of DNA in a process to locally transfect a cell or a cellular process via transfection. The DNA can be contained in a vector.

The invention includes an isolated DNA encoding a protein operably linked to a nucleic acid comprising a promoter/regulatory sequence such that the nucleic acid is preferably capable of directing expression of the protein encoded by the nucleic acid. Thus, the invention encompasses expression vectors and methods for the introduction of exogenous DNA into cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

Expression of a protein in a cell or a cellular process transfected as disclosed herein may be accomplished by generating a plasmid or other type of vector comprising the desired nucleic acid operably linked to a promoter/regulatory sequence which serves to drive expression of the protein, with or without a tag, in cells in which the vector is introduced. Many promoter/regulatory sequences useful for driving constitutive expression of a gene are available in the art and include, but are not limited to, for example, the cytomegalovirus immediate early promoter enhancer sequence, the SV40 early promoter, as well as the Rous sarcoma virus promoter, and the like. Moreover, inducible and tissue specific expression of the nucleic acid encoding a protein can be accomplished by placing the nucleic acid encoding a protein under the control of an inducible or tissue specific promoter/regulatory sequence. Examples of tissue specific or inducible promoter/regulatory sequences which are useful for his purpose include, but are not limited to the MMTV LTR inducible promoter, and the SV40 late enhancer/promoter. In addition, promoters which are well known in the art which are induced in response to inducing agents such as metals, glucocorticoids, and the like, are also contemplated in the invention. Thus, it will be appreciated that the invention includes the use of any promoter/regulatory sequence, which is either known or unknown, and which is capable of driving expression of the desired protein operably linked thereto.

Selection of any particular plasmid vector or other DNA vector is not a limiting factor in this invention and a wide plethora of vectors are well-known in the art. Further, it is well within the skill of the artisan to choose particular promoter/regulatory sequences and operably link those promoter/regulatory sequences to a DNA sequence encoding a desired polypeptide. Such technology is well known in the art and is described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The nucleic acids encoding a protein can be cloned into various plasmid vectors. However, the present invention should not be construed to be limited to plasmids or to any particular vector. Instead, the present invention should be construed to encompass a wide plethora of vectors which are readily available and/or well-known in the art.

The present invention further comprises locally transfecting an inhibitory nucleic acid, such as an antisense nucleic acid, an siRNA or an miRNA into a cell. An siRNA polynucleotide is an RNA nucleic acid molecule that interferes with RNA activity that is generally considered to occur via a post-transcriptional gene silencing mechanism. An siRNA polynucleotide preferably comprises a double-stranded RNA (dsRNA) but is not intended to be so limited and may comprise a single-stranded RNA (see, e.g., Martinez et al., 2002, Cell 110:563-74). The siRNA polynucleotide included in the invention may comprise other naturally occurring, recombinant, or synthetic single-stranded or double-stranded polymers of nucleotides (ribonucleotides or deoxyribonucleotides or a combination of both) and/or nucleotide analogues as provided herein (e.g., an oligonucleotide or polynucleotide or the like, typically in 5' to 3' phosphodiester linkage). Accordingly it will be appreciated that certain exemplary sequences disclosed herein as DNA sequences capable of directing the transcription of the siRNA polynucleotides are also intended to describe the corresponding RNA sequences and their complements, given the well-established principles of complementary nucleotide base-pairing.

An siRNA may be transcribed using as a template a DNA (genomic, cDNA, or synthetic) that contains a promoter for an RNA polymerase promoter. For example, the promoter can be the U6 promoter or the H1 RNA polymerase III promoter. Alternatively, the siRNA may be a synthetically derived RNA molecule. In certain embodiments, the siRNA polynucleotide may have blunt ends. In certain other embodiments, at least one strand of the siRNA polynucleotide has at least one, and preferably two nucleotides that "overhang" (i.e., that do not base pair with a complementary base in the opposing strand) at the 3' end of either strand of the siRNA polynucleotide. In a preferred embodiment of the invention, each strand of the siRNA polynucleotide duplex has a two-nucleotide overhang at the 3' end. The two-nucleotide overhang is preferably a thymidine dinucleotide (TT) but may also comprise other bases, for example, a TC dinucleotide or a TG dinucleotide, or any other dinucleotide. The overhang dinucleotide may also be complementary to the two nucleotides at the 5' end of the sequence of the polynucleotide that is targeted for interference. For a discussion of 3' ends of siRNA polynucleotides see, e.g., WO 01/75164.

Preferred siRNA polynucleotides comprise double-stranded polynucleotides of about 18-30 nucleotide base pairs, preferably about 18, about 19, about 20, about 21, about 22, about 23, about 24, about 25, about 26, or about 27 base pairs, and in other preferred embodiments about 19, about 20, about 21, about 22 or about 23 base pairs, or about 27 base pairs. The siRNA polynucleotide useful in the present invention may also comprise a polynucleotide sequence that exhibits variability by differing (e.g., by nucleotide substitution, including transition or transversion) at one, two, three or four nucleotides from a particular sequence. These differences can occur at any of the nucleotide positions of a particular siRNA polynucleotide sequence, depending on the length of the molecule, whether situated in a sense or in an antisense strand of the double-stranded polynucleotide. The nucleotide difference may be found on one strand of a double-stranded polynucleotide, where the complementary nucleotide with which the substitute nucleotide would typically form hydrogen bond base pairing, may not necessarily be correspondingly substituted. In preferred embodiments, the siRNA polynucleotides are homogeneous with respect to a specific nucleotide sequence.

Polynucleotides that comprise the siRNA polynucleotides may in certain embodiments be derived from a single-stranded polynucleotide that comprises a single-stranded oligonucleotide fragment (e.g., of about 18-30 nucleotides) and its reverse complement, typically separated by a spacer sequence. According to certain such embodiments, cleavage of the spacer provides the single-stranded oligonucleotide fragment and its reverse complement, such that they may anneal to form, optionally with additional processing steps that may result in addition or removal of one, two, three or more nucleotides from the 3' end and/or the 5' end of either or both strands, the double-stranded siRNA polynucleotide of the present invention. In certain embodiments the spacer is of a length that permits the fragment and its reverse complement to anneal and form a double-stranded structure (e.g., like a hairpin polynucleotide) prior to cleavage of the spacer, and optionally, subsequent processing steps that may result in addition or removal of one, two, three, four, or more nucleotides from the 3' end and/or the 5' end of either or both strands. A spacer sequence may therefore be any polynucleotide sequence as provided herein that is situated between two complementary polynucleotide sequence regions which, when annealed into a double-stranded nucleic acid, result in an siRNA polynucleotide.

The present method further comprises methods for introducing a nucleic acid into a cell. The method comprises transfecting a cell in the presence of a nucleic acid, preferably RNA and/or DNA, where the nucleic acid is in a fluid medium permitting the transfer of the nucleic acid from one side of the cell membrane to the other side of the cell membrane through the cell membrane. The fluid medium can comprise any medium having the buffering capacity and pH to support the viability of a cell and the stability of a nucleic acid molecule. Contemplated media include, but are not limited to, phosphate buffered saline, Tris, Tris-EDTA (TE) cell culture media, other aqueous mediums and buffers, and the like.

The number of nucleic acid molecules that enter the cell is influenced by the nucleic acid concentration in the nucleic acid bath, the size of the nucleic acid molecule, and, with photo transfection, the laser intensity, e.g., the length of each laser pulse and the number of laser pulses delivered. Based on the teachings herein, the skilled artisan can readily adjust the parameters of the transfection process to control the approximate number of nucleic molecules that enter the cell.

In one embodiment, a cell is surrounded by an nucleic acid bath comprising a nucleic acid molecule, preferably an RNA molecule, at about 1 to about 150 µg/ml, more preferably about 10 to about 100 µg/ml, and more preferably still at about 10 to about 50 µg/ml in the bath.

In another embodiment, a cell is bathed in discrete locations on the cell surface with a solution comprising a nucleic acid molecule. For instance, using a patch pipette, micropipette or other applicator, a solution comprising nucleic acid is applied to a discrete location on the surface of a cell. The solution may be applied to more than one location on a cell. If phototransfection is employed, the cell is then irradiated using a laser at one or more sites within a discrete location. Nucleic acid in the solution is present at about 1 nanogram per microliter (ng/µl) to about 2 microgram/microliter (µg/µl), preferably about 50 ng/µl to about 1 µg/µl, and more preferably about 100 ng/µl to about 500 ng/µl.

The present invention further comprises the use of other methods for introducing a nucleic acid to a cell, tissue or animal via transfection. Methods included in the present invention include, for example, perfusion, picospritzing, microinjection and the like. Methods for perfusion include, but are not limited to, using a pump to move a fluid medium comprising a nucleic acid, preferably RNA, even more preferably mRNA, to a cell, tissue or animal. The fluid medium used in the perfusion methods of the present invention can included those disclosed elsewhere herein, such as buffered solutions that support and maintain the stability of a nucleic acid and a cell, tissue or animal. In one embodiment of the present invention, the fluid medium can include a medium, such as Basal Media Eagle (BME), BGJb Medium, Brinster's BMOC-3 Medium, CMRL Medium, $CO_2$-Independent Medium, Dulbecco's Modified Eagle Media (D-MEM), F-10 Nutrient Mixtures, F-12 Nutrient Mixtures, Glasgow Minimum Essential Media, Grace's Insect Cell Culture Media, Improved MEM, IPL-41 Insect Media, Iscove's Modified Dulbecco's Media, Leibovitz's L-15 Media, McCoy's 5A Media (modified), MCDB 131 Medium, Media 199, Medium NCTC-109, Minimum Essential Media (MEM), Modified Eagle Medium (MEM), Opti-MEM® I Reduced Serum Media, RPMI Media 1640, Schneider's *Drosophila* Medium, Waymouth's MB 752/1 Media, Williams Media E, artificial spinal fluid (aCSF), Ringer's solution and the like. The present invention can further comprise the use of buffered salt solutions, including, but not limited to, Dulbecco's Phosphate-Buffered Saline (D-PBS), Earle's Balanced Salt Solution, Hanks' Balanced Salt Solution, Phosphate-Buffered Saline (PBS), and the like.

The present invention further comprises using picospritzing in conjunction with phototransfection to introduce a nucleic acid to a cell, organ or tissue. Picospritzing comprises the use of electrical pulses with a pressure device to deliver a compound, such as a nucleic acid, to a cell, tissue or animal. Method for picospritzing are known in the art and are described in, for example, Herberholz, et al., 2002, J. Neuroscience, 22: 9078-9085). Picospritzing apparatuses are available from, for example, World Precision Instruments (Sarasota, Fla.).

In another embodiment, transfection of cells with nucleic acids encoding two or more different polypeptides is effected by microinjection.

When phototransfection is employed, the methods comprise irradiating a cell with a laser to phototransfect and locally transfect the cell. When the laser contacts the cell membrane, or cell wall in the case of plant cells, fungal cells, and other cells comprising a cell wall, the plasma membrane or cell wall is perforated, permitting the diffusion of foreign molecule, such as RNA and/or DNA, to enter the cell. The fluidity of mammalian cell membranes facilitates subsequent closure of the perforation. Lasers compatible with the present invention include, but are not limited to, continuous-wave argon-ion lasers operating at 488 nm (Schneckenburger, et al., 2002, J. Biomed. Opt., 7: 410-416; Palumbo et al., 1996, J. Photochem. Photobiol. B-Biol., 36: 41-46), pulsed and frequency upconverted Nd:YAG lasers operating at 355 nm (Shirahata, et al., 2001, J. Invest. Med., 49: 184-190), 532 nm (Soughayer, et al., 2000, Anal. Chem., 72: 1342-1347), and 1064 nm (Mohanty, et al., 2003, Biotechnol. Lett. 25: 895-899), and femtosecond titanium-sapphire lasers (Tirlapur, et al., 2002, Plant J. 31: 365-374; Tirlapur, et al., 2002, Nature 418: 290-291; Zeira, et al., 2003, Mol. Therapy 8: 342-350). Preferably, a titanium-sapphire laser at 405 nm (PicoQuant GmbH, Berlin Germany) is used to phototransfect a cell. However, the present invention is not limited to the a titanium-sapphire laser, but includes any laser with the capacity of delivering a localized focal volume of about $10^{-19}$ m$^3$.

Control of the incident laser beam is achieved by using various apparatuses to control the focus and power of the laser, as well as to aim the laser. Focusing the laser is achieved by passing the incident laser through a lens, such as a microscope lens, placed between the laser and the cell. The power of the laser in controlled by modulating the voltage and current going to the laser and through the use of neutral density filters or pockels cells. Exposure of the cells to the laser is controlled through a shutter, such as a single lens reflex (SLR) camera shutter and/or with electronically controlled pockels cells.

Aiming the laser is accomplished through a microscope lens and with dielectric and steering mirrors and AOD (acoustic optical deflector) between the laser source and a cell. A microscope useful in the practice of the present invention includes, but is not limited to, a confocal microscope, a multiphoton excitation fluorescence microscope, a light microscope, and the like. The present method further comprises aiming the laser using an optical fiber to transmit the laser to a distant or difficult-to-access area. As a non-limiting example, an optical fiber is used to phototransfect intestinal, neural or cardiothoracic cells in a live animal. Further, the present invention comprises phototransfecting a cell or a population of cells using multiple optical fibers in an animal. Optical fibers are well known in the art and are described in, for example, U.S. Pat. Nos. 3,711,262 6,973,245.

A laser beam with less than a milliwatt of power for tens of milliseconds is sufficient to porate a cell (Paterson, et al., 2005, Optics Express, 13: 595-600). Preferably, the laser has a power density of about 1200 MWm$^{-2}$ and a total power of about 30-55 mW at the back aperture of the lens. Further, in order to provide maximum surface area for transfection, the laser beam should be highly circular (dx=dy) with beam diameter of about 2 mm.

The starting power output of the laser is attenuated through the use of various filters, such as a neutral density (ND) filter to reduce the power to the milliwatt range required for phototransfection with no attendant pathological effects on the target cell. The beam can be expanded through the use of a telescope where f=100 mm, and directed into a microscope, such as a light microscope or an oil-immersion microscope with a ×100 objective (N.A.=1.25). An SLR shutter between the laser source and the microscope permits control of the exposure time. An exposure time of about 40 ms is sufficient to porate a cell without attendant damage, but this parameter can be altered to increase or decrease exposure time.

Target cells in a nucleic acid bath are positioned and focused on by manipulating the stage of the microscope and/or using dielectric and steering mirrors and AOD, so the beam is focused on the cell membrane and not towards the nucleus of the cell. When porating a cellular process, such as a dendrite, the beam is focused directly on the cellular process.

An exemplary phototransfection protocol comprises at least two and preferably three sequential phototransfection steps of a recipient cell using the transcriptome, preferably the mRNA transcriptome, from a donor cell. The mRNA transcriptome comprises a range of mRNA sizes and has an average transcript size between about 1 to 3.5 kb. The first phototransfection step is at about 35 mW using a titanium-sapphire laser and subsequent phototransfections steps are at a lower power, such as 30 mW or less. Each phototransfection step involves laser irradiating the recipient cell at numerous, random sites. The number of sites per step is determined by consideration of the strength of the laser, the diameter of the pores that result in the irradiated site, the average size of the transcripts in the mRNA transcriptome and modeling transport of individual transcripts through the pore using Brownian dynamics. After the first phototransfection step, the recipient cell may be transferred to a growth medium specific for the donor cell.

In some embodiments, the cells are transfected with a nucleic acid comprising a marker that indicates a successful transfection. Such markers are known in the art and include, for example, antibiotic resistance and fluorescent proteins. Successful transfection can be tracked by the addition of a detectable molecule to the nucleic acid solution. Such molecules are well known in the art. Preferably, the molecule is non-toxic to the recipient cell. Non-limiting examples include Lucifer yellow and carboxyfluorescein diacetate succinimidyl ester. Expression of the locally transfected nucleic acid is analyzed according to the presence and activity of a marker or the phenotype of the cell.

EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1: Transdifferentiation of Fibroblast to tCardiomyocyte

Cardiomyocyte-like cells ("tCardiomyocytes") were created from mouse primary embryonic fibroblasts using the following materials and methods.

Cell Culture and Poly-A+RNA Transfection

Primary mouse embryonic fibroblast (PMEF-NL; Millipore) culture was incubated in DMEM supplemented with 10% FBS at 37° C. with 5% CO2. WT adult mouse (strain C57BL/6, 7-9 wk old) ventricular myocytes were isolated from hearts mounted on a Langendorf apparatus and perfused with Ca2+-free Tyrode's solution with collagenase B and D plus protease. The ventricle was dissected, and sections of ventricle tissue were gently triturated to dissociate individual myocytes. Mouse cortical astrocytes were isolated from mouse embryos and cultured in DMEM supplemented with 10% FBS. AVM poly-A+RNA was isolated using TRIzol and the Micro-FastTrack 2.0 Kit (Invitrogen), following the manufacturer's protocol. There were two transfection protocols. First, cell transcription was inhibited by adding 80 μM 5,6-dichloro-1-β-D-ribofuranosylbenzimidazole for 30 min before transfection. Transcription inhibitor-treated cells were transfected with 2 μg of poly-A+ RNA per 35-mm culture dish using the TransMessenger Transfection Reagent Kit (Qiagen) following the manufacturer's protocol. Second, cells were incubated with 80 μM 5,6-dichloro-1-β-D-ribofuranosylbenzimidazole for 6 h, after which cells that had detached from the bottom were collected by centrifugation. The collected cells were transfected with 4 μg of poly-A+RNA using Lipofectamine 2000 (Invitrogen). Transfected cells were retransfected at 2-7 d after the first transfection using the TransMessenger Transfection Reagent Kit. Primary mouse embryonic fibroblast poly-A+RNA was used as a control transfection. The media was changed every 2-3 d, and growth was observed under a light microscope. Live cell images were obtained using the Zeiss LSM510 or LSM 710 Microscope System. Cell length and width were measured by drawing straight lines encompassing nuclei on live cell images using MetaMorph software (Molecular Devices).

Immunocytochemistry

Cells were fixed in 4% paraformaldehyde for 5 min and permeablized in cold methanol for 10 min at −20° C. The fixed cells were incubated in blocking solution (10% goat serum in PBS) for 30 min at room temperature and then incubated overnight in primary antibodies (1:500 dilution in 1% goat serum in PBS) at 4° C. Alexa Fluor 488- or Alexa Fluor 568-conjugated secondary antibodies (1:500 dilution in 1% goat serum in PBS) were used to label primary antibodies. Immunostained cells were mounted on glass slides using DAPI-containing mounting medium. Images were captured with the Zeiss LSM 510 or LSM 710 microscope system.

Single Cell Microarray

Poly-A+RNAs of single cells were isolated and amplified following the standard single-cell harvesting and aRNA amplification method (1990, Van Gelder et al., Proc Natl Acad Sci USA 87:1663-1667). Amplified single-cell aRNAs (three or four rounds of amplification) were used to probe the Affymetrix GeneChip Mouse Genome 430 2.0 array. Data were analyzed using the R/Bioconductor package and Gene-Spring GX version 11 (Agilent) (2003, Irizarry et al., Nucleic Acids Res 31:e15; 2004, Gentleman et al., Genome Biol 5:R80). The second-highest intensity values were extracted from the probe sets, and informative probe sets were selected based on their ability to distinguish AVMs from fibroblasts. Individual t tests were performed for each probe set, contrasting AVM expression (n=4) and fibroblast expression (n=3), and the 3,257 probe sets with expression differing significantly between the two cell types ($P<0.05$) were retained. Hierarchical clustering was performed on these 3,257 probe sets across all cell types (four AVMs, three fibroblasts, five cardio-TIPeR cells, and three fibro-TIPeR cells), using Euclidean distance and the complete linkage method. Bootstrap values were calculated using the R pvclust package; unbiased P values for 1,000 times resampling support of the tree were reported. Heat maps were produced using the heat map.2 routine in the R gplots package, focusing on gene subsets for which successfully converted tCardiomyocytes had significantly ($P<0.1$) different expression than untreated fibroblasts by the t test on each probe set. These lists were filtered to exclude probe sets with very similar expression (less than a twofold difference) between AVMs and fibroblasts, as well as probe sets for genes that appeared to be induced by the treatment effect [probe sets showing a significant ($P<0.05$) expression difference between fibroblasts and the fibroblast treatment controls]. Gene Ontology enrichment analysis was performed using the DAVID Bioinformatics Resources 6.7 Web site (2003, Dennis et al., Genome Biol 4:P3; 2009, Huang et al., Nat Protoc 4:44-57).

Electrophysiology and $Ca^{2+}$ Imaging

Patch clamp recordings were performed using the patch clamp technique in the whole-cell configuration as described previously (29). In brief, GΩ seals were achieved using pipettes fashioned from borosilicate glass (WPI) with resistances of 2-3 MΩ after fire polishing. Recordings were obtained from putative tCardiomyocytes at 25° C. using a resistive heater system (Warner Instruments). Action potentials were elicited using an Axopatch 200B amplifier (Molecular Devices) by injecting 0.4 to 0.5-nA pulses at 1-3 Hz with a 0.2- to 0.3-ms duration controlled by a Pentium 4-based PC running the pClamp program (v. 9.2; Molecular Devices). Voltage recordings were filtered at 1-2 kHz and digitized at 25 kHz using the Digidata 1332A A/D converter (Molecular Devices). Two solutions were used for current clamp recordings: pipette solution (80 mM K+-aspartate, 50 mM KCl, 1 mM MgCl2, 10 mM EGTA, 10 mM Hepes, and 3 mM Mg2+ATP, pH-adjusted to 7.2 with KOH) and bath solution (132 mM NaCl, 4.8 mM KCl, 1.2 mM CaCl2, 2 mM MgCl2, 10 mM Hepes, and 5 mM glucose, pH-adjusted to 7.4 with NaOH). Cytosolic free Ca2+ changes were monitored as follows. Fluo 4-AM (5 μg/mL in the bath solution) (Invitrogen) was loaded into cultures for 40 min, washed three times in the bath solution, and de-esterified for 15 min at room temperature. Fluo 4-AM-loaded cells were observed with the Zeiss LSM 710 system at 2- to 3-s intervals (1993, Cheng et al., Science 262:740-744).

The results of the experiments are now described.

Generation of tCardiomyocytes from Fibroblasts Using Transcriptome Transfer

TIPeR generation of the desired cardiomyocyte phenotype requires an available source of cardiomyocyte RNA. Poly-A+RNA was isolated from ventricular myocytes from adult mice (7-9 wk old) and transfected 2 μg of poly-A+ RNA per 35-mm culture dish into primary mouse embryonic fibroblast cells at passage 3 using cationic lipids. The transfected cultures were monitored daily for recovery and status. A second transfection was performed at varying intervals (3-7 d) after the first transfection. These TIPeR cells are referred to as cardio-TIPeR cells. As a control for RNA addition and transfection, fibroblast poly-A+RNA was transfected into fibroblast cultures (fibro-TIPeR), using the same transfection procedure. A cell was considered to be a tCardiomyocyte (cardiomyocyte transcriptome-effected cell) once a cardio-TIPeR cell expressed any of the cardiomyocyte phenotype from a single-cell phenotyping procedure. Within 2 wk after the first transfection, the overall morphology of individual cardio-TIPeR cells exhibited a morphology distinct from that of fibroblasts that further discriminated tCardiomyocytes from noneffected cardio-TIPeR cells. Compared with fibroblasts, tCardiomyocytes were more 3D under DIC imaging, with an increased elongated or triangular shape (FIG. 1, DIC images). A subpopulation of tCardiomyocytes exhibited a triangular shape similar to that of neonatal cardiomyocytes, whereas other tCardiomyocytes had an elongated rod shape similar to adult cardiomyocytes. The corresponding fibro-TIPeR cells appeared to be larger with a flat morphology indistinguishable from fibroblasts. Cell morphology analysis measuring the ratio of maximum cell length to minimum cell width showed that the subpopulation of cardio-TIPeR cells was distinct from the fibroblast cluster (low length-to-width ratio) and grouped with adult ventricular myocytes (AVMs) (high length-to-width ratio) (FIG. 1, graph). This result indicates that cardio-TIPeR cells develop morphology distinct from that of fibroblasts and fibro-TIPeR cells. The time lapse between transfection and the emergence of tCardiomyocyte morphologies suggests a requisite time dependence associated with these morphological changes. The diversity of cell morphologies (neonatal or adult cardiomyocyte-like) implies that a range of gene expression profiles is formed with the introduction and subsequent action of the donor transcriptome. The action of the donor transcriptome occurs in the context of the endogenous host transcriptome that varies among host cells. Although similar phenotypes exist among fibroblasts, the gene expression profiles are not identical; this applies to AVMs as well. These observations are consistent with the initiation and maintenance of a cell reprogramming process varying depending on the host cell expression profile (i.e., relative abundance of gene products).

tCardiomyocyte Expression of Cardiomyocyte Antigenic Markers.

Figure 2:
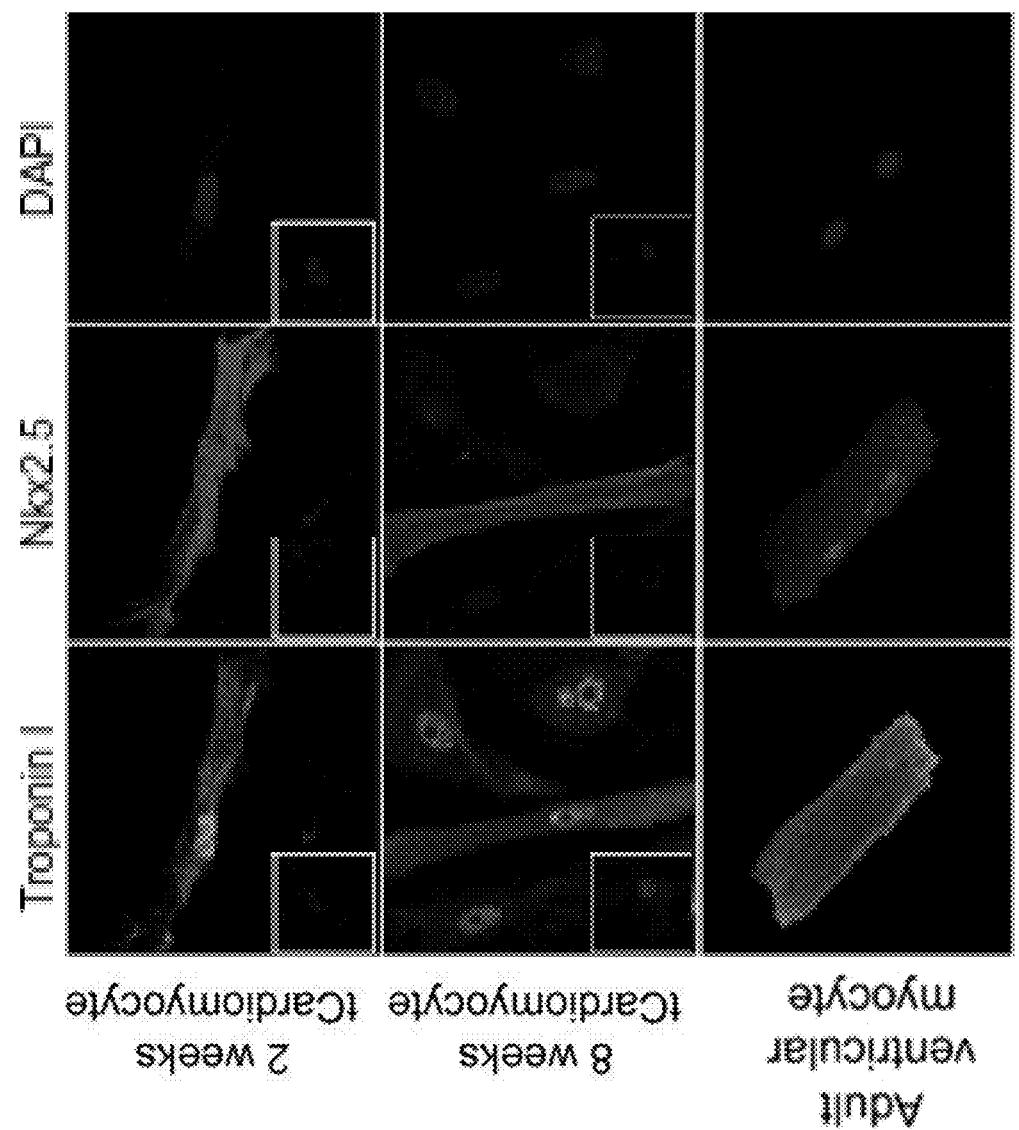
FIG. 2 depicts the results of experiments demonstrating that tCardiomyocytes express cardiac antigenic markers continuously. tCardiomyocytes and fibro-TIPeR cells are double-immunostained with anticardiac troponin I antibody (left column) and anti-Nkx2.5 antibody (middle column). tCardiomyocytes show similar expression patterns of cardiac antigenic markers as adult ventricular myocytes from 2 wk to 8 wk of incubation. (Insets) Immunostaining results of corresponding fibro-TIPeR cells.

The expression of cardiac markers in tCardiomyocytes was assessed, specifically the cardiac muscle component cardiac troponin I and transcription factor Nkx2.5, by immunocytochemistry (FIG. 2). The expression of cardiac markers was observed at 2 wk posttransfection (FIG. 2, first row) and was stable for the duration of the 8-wk culturing period (FIG. 2, second row). The subcellular distribution of cardiac markers was similar in AVMs and tCardiomyocytes. The immunocytochemistry results were consistent with the cell morphology results; both changes were detected at 2 wk after the first transfection and persisted for more than 8 wk in morphologically distinctive cells.

Reprogramming of Global Gene Expression in tCardiomyocytes

Figure 3A:
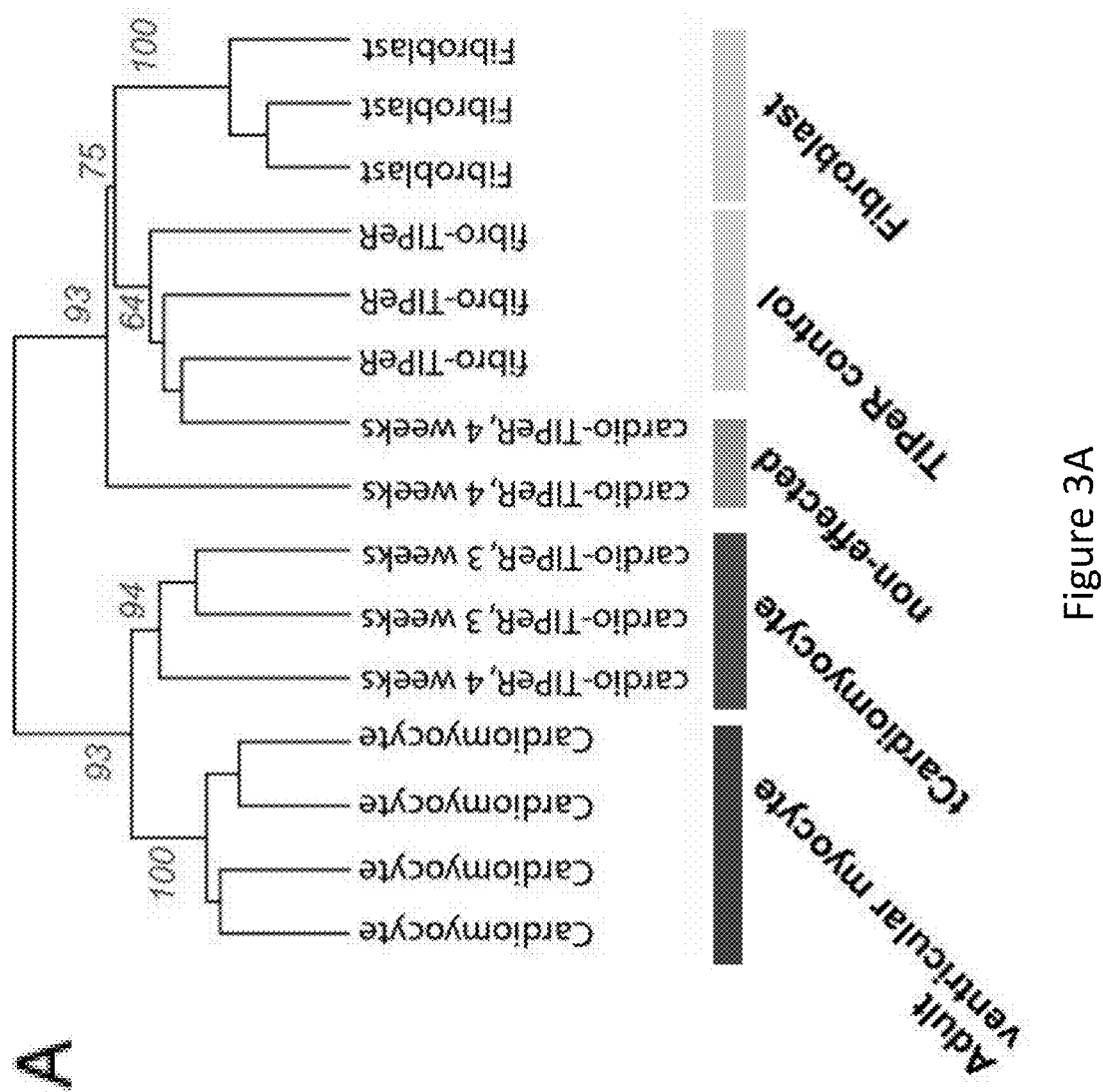
FIGS. 3A and 3B, depicts the results of experiments demonstrating that global gene expression of tCardiomyocytes is reprogrammed toward adult ventricular myocytes. (3A) Dendrogram showing hierarchical clustering (Euclidean distance, complete linkage) of single AVMs, fibroblasts, cardio-TIPeR, and fibro-TIPeR using the expression values of 3,257 informative genes. Bootstrap values from 1,000 times resampling are shown. (3B) Heat map showing cardiomyocyte-specific genes that are up-regulated in the tCardiomyocytes (n=262) and fibroblast-specific genes that are downregulated in the tCardiomyocytes (n=136). Relevantly enriched Gene Ontology categories are annotated.
Figure 3B:
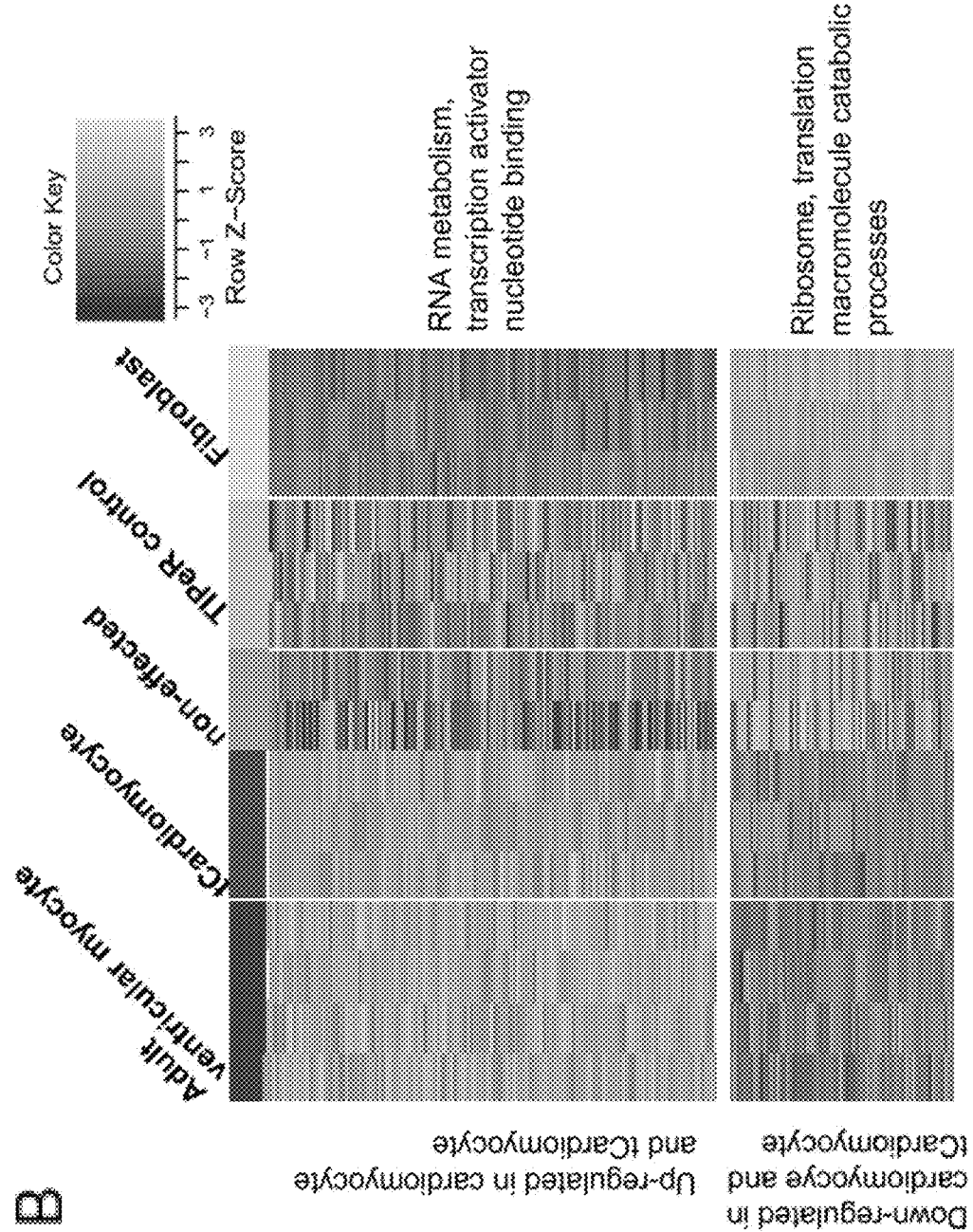

To assess global gene expression changes, the transcriptome profiles of single tCardiomyocytes was compared with single fibroblasts, AVMs, and fibro-TIPeR cells. Single-cell RNA was harvested by capillary-mediated aspiration. Poly-A+RNA was amplified using an aRNA amplification procedure and used as a probe to screen Affymetrix Mouse Genome 430 2.0 microarrays. An informative group of 3,257 probe sets, differentially expressed between fibroblasts and AVMs, was selected and analyzed to compare gene expression profiles between single tCardiomyocytes and other single cells (FIG. 3A). Hierarchical clustering analysis showed that three out of five cardio-TIPeR cells (60%) were clustered with AVMs, one cardio-TIPeR cell was located with fibro-TIPeR cells, and the remaining cardio-TIPeR cells were located between the fibroblast group and the AVM-tCardiomyocyte group. Bootstrap resampling (1,000 times) resulted in the grouping of tCardiomyocytes and AVMs with 93% support. Along with an increase in gene expression for genes traditionally thought to be AVM-enriched, a decrease in fibroblast enriched gene expression also would be expected. This was seen in the cells that had transitioned from the fibroblast phenotype to the tCardiomyocyte phenotype (FIG. 3B).

tCardiomyocytes Function as an Electrically Excitable Cell

Figure 4A:
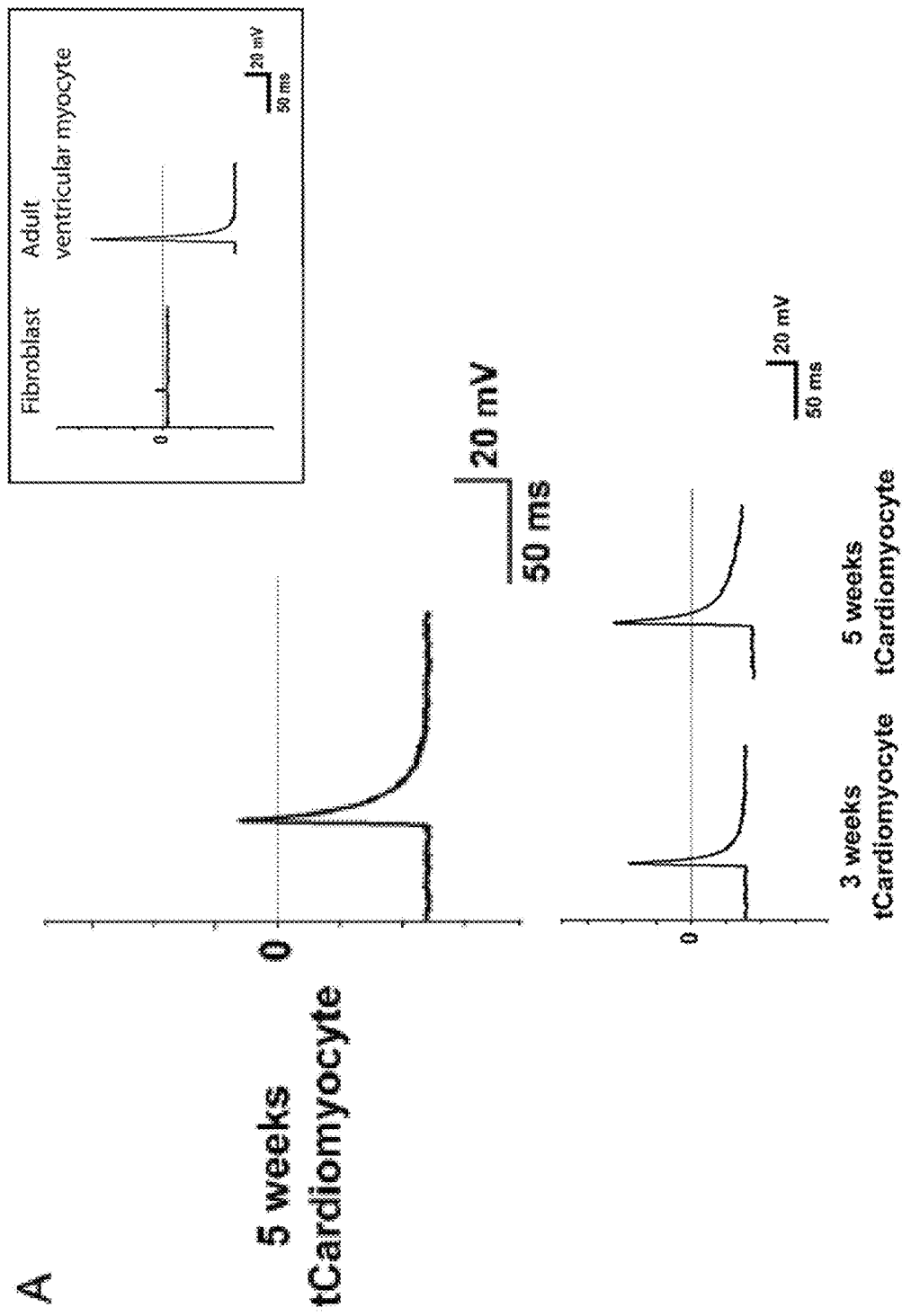
FIGS. 4A and 4B, depicts the results of experiments measuring the electrical properties of tCardiomyocytes. tCardiomyocytes gain electrical functions similar to adult ventricular myocytes. (4A) tCardiomyocyte expresses stereotypical cardiac action potential (first row). Other tCardiomyocytes display a more diverse pattern of action potential profiles. (Inset) Patch clamp results of fibroblasts and adult ventricular myocytes. (4B) tCardiomyocytes show intracellular local Ca2+ oscillations. Local areas are selected (white dashed circles) and local Ca2+ changes are recorded (line graphs) by time course.
Figure 4B:
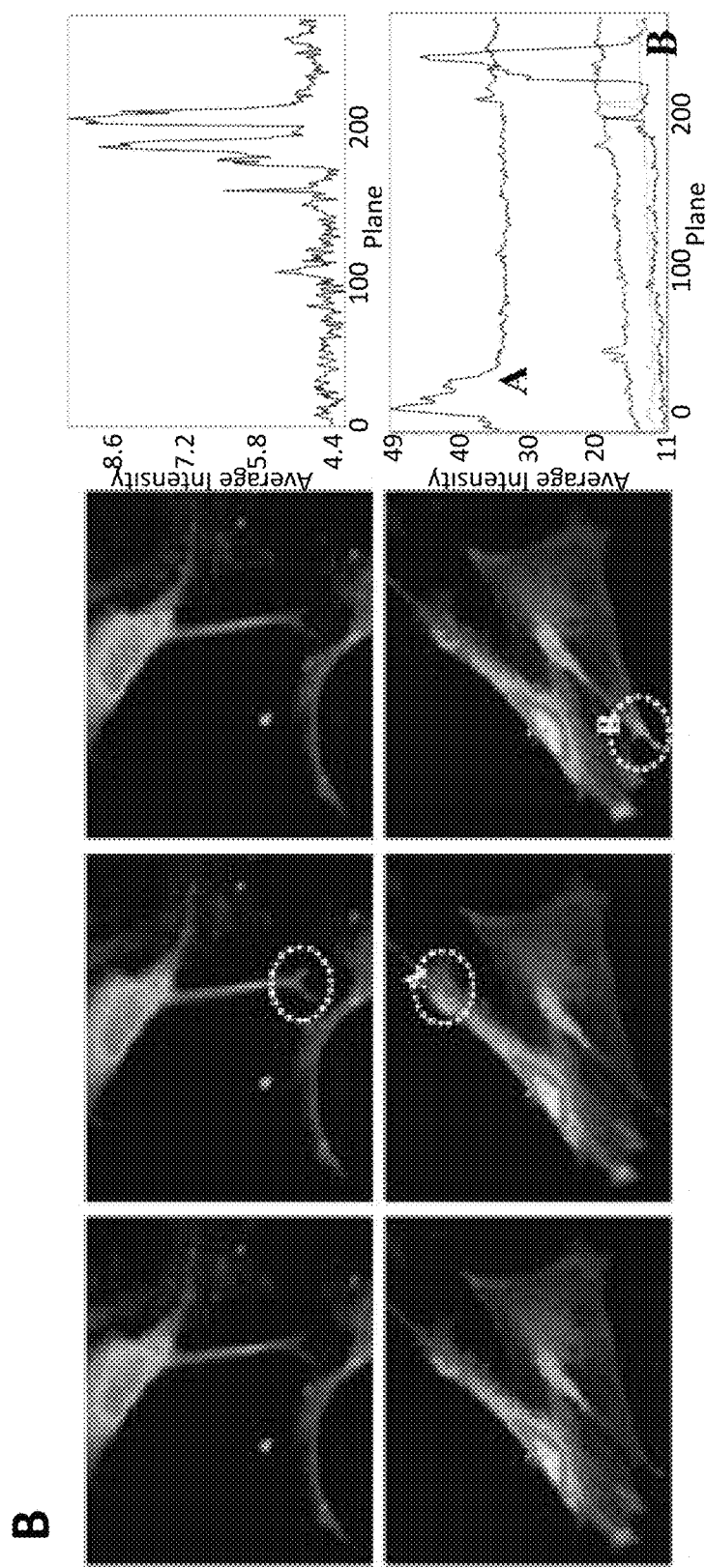

Because cardiomyocytes are electrically excitable, tCardiomyocytes were assessed for excitability using the patch clamp technique (FIG. 4A). It was found that action potentials could be elicited from tCardiomyocytes, and that these voltage recordings were similar to those obtained from isolated mature ventricular myocytes (FIG. 4A, first row). tCardiomyocytes had identical resting potentials (−50 mV), with similar upstroke and repolarization patterns, as mature adult ventricular myocytes, although the peak amplitude of the action potentials from tCardiomyocytes was slightly lower than that from isolated mature ventricular myocytes. Action potentials were recorded in 10 out of 16 clamped cardio-TIPeR cells (62.5%). Resting membrane potentials ranged from −55 mV to −10 mV, and membranes were instantly depolarized with electric stimulation. The peak amplitudes and repolarization rates varied among tCardiomyocytes. These varying electrophysiological characteristics suggests that each tCardiomyocyte might have a unique composition of ion channel types and abundances conferring differing electrical properties (2007, Harrell et al., Physiol Genomics 28:273-283). In separate experiments, but in accordance with the action potential data, we also observed cytosolic $Ca^{2+}$ concentration changes in tCardiomyocytes (FIG. 4B). tCardiomyocytes demonstrated intracellular local $Ca^{2+}$ oscillations without stimulation (1991, Harootunian et al., Science 251:75-78; 1993, Cheng et al., Science 262: 740-744).

Generation of tCardiomyocytes from Mouse Astrocytes

Figure 5A:
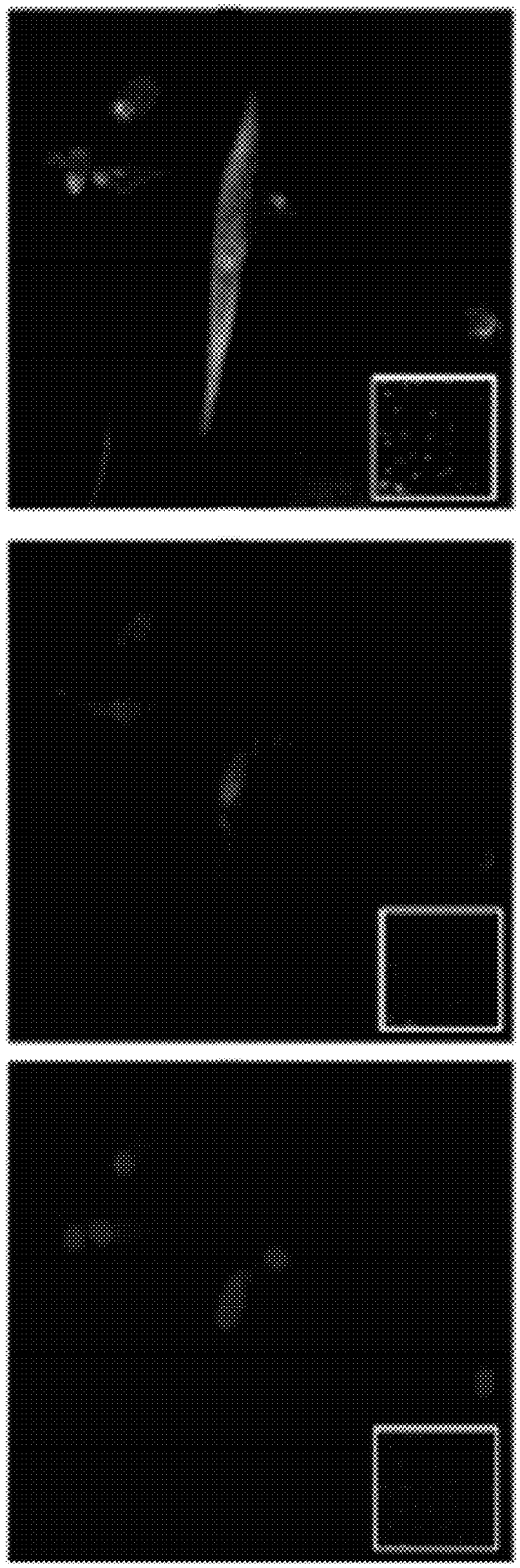
FIGS. 5A and 5B, depicts the results of experiments demonstrating that tCardiomyocytes generated from mouse astrocytes show phenotypic characteristics of AVMs. (5A) Astrocyte-generated tCardiomyocytes (3 wk after the transfection) double-immunostained with anti-troponin I antibody (Top) and anti-Nkx2.5 antibody (Middle). Nuclei are shown at bottom. (Insets) Immunostaining results of corresponding mock-transfected astrocytes. (5B) Dendrogram and heat map showing hierarchical clustering (Pearson distance, complete method) of single AVMs, astrocyte-generated tCardiomyocytes, and astrocytes (4 wk after the transfection). Differentially expressed 1,690 informative genes are selected by P value cutoff (P<0.01). Bootstrap values (%) from 1,000 resamplings are shown at each node.
Figure 5B:
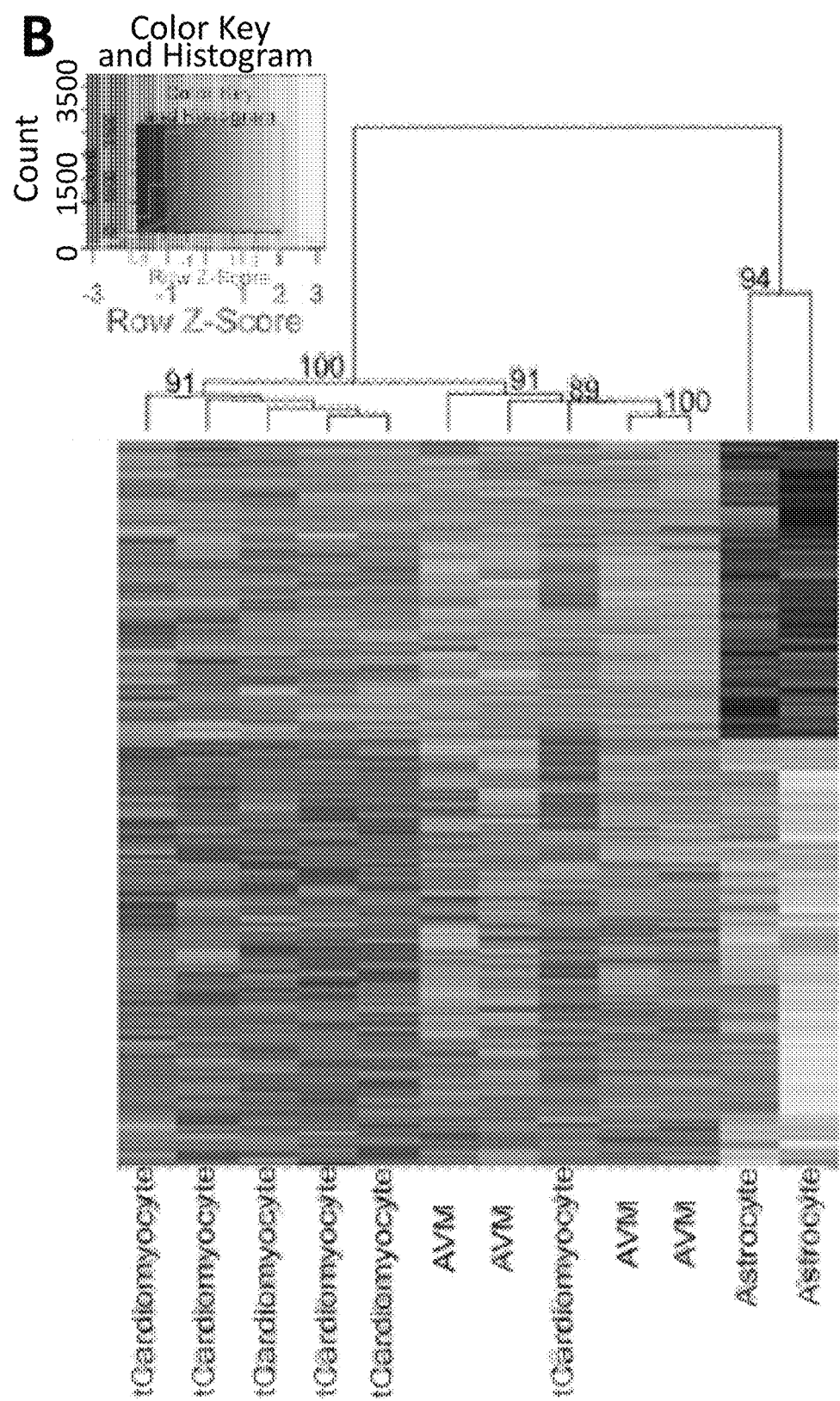

To examine the dependency of tCardiomyocyte generation on host cell type, AVM poly-A+RNAs were transfected into primary mouse cortical astrocyte cultures using the identical procedures used for the fibroblast cultures. Cardio-TIPeR astrocyte cultures showed similar progression as seen in cardio-TIPeR fibroblast cultures. The subset of cardio-TIPeR astrocytes showed elevated and elongated cell morphologies at 2 wk after the first transfection. Expression of cardiac troponin I and Nkx2.5 was observed in astrocyte-generated tCardiomyocytes that displayed elongated cell morphology (FIG. 5A). In addition to the immunocytochemistry staining, global gene expression changes were examined in astrocyte-generated tCardiomyocytes (FIG. 5B). A group of informative 1,690 probe sets, differentially expressed between AVMs and tCardiomyocytes versus mock-transfected astrocytes (P<0.01), was selected and analyzed further. All six AVM mRNA transfected astrocyte single cells were grouped with single AVMs with 100% bootstrap support from 1,000 resamplings. It should be noted that one of the tCardiomyocytes was clustered within the AVM group, demonstrating that this tCardiomyocyte is further along the transdifferentiation pathway then some of the other cells by virtue of sharing a more similar global gene expression profile with single AVMs.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of effecting phenotype conversion in a cell, said method comprising introducing phenotype-converting nucleic acid of a first cell having a phenotype into a second cell having a phenotype, wherein the phenotype-converting nucleic acid comprises at least one RNA, wherein the phenotype of said first cell is different from the phenotype of said second cell, wherein the second cell is pre-treated with a transcription inhibitor before it is transfected, wherein said transfected phenotype-converting nucleic acid causes the phenotype of said second cell to change to the phenotype of said first cell, and wherein said phenotype-converting nucleic acid is locally administered to said second cell in vivo.

2. The method of claim 1, wherein said phenotype-converting nucleic acid is an mRNA transcriptome.

3. The method of claim 1, wherein said phenotype of said first cell differs from said phenotype of said second cell by one or more of: differentiation degree, disease state, exposure to a toxin, exposure to a pathogen, and exposure to a candidate therapeutic.

4. The method of claim 2, wherein said mRNA transcriptome comprises mRNA transcripts having an average size between about 1 kb to about 5 kb.

5. The method of claim 2, further comprising introducing said second cell at least a second time with said first cell mRNA transcriptome.

6. The method of claim 1, wherein said first cell is a cardiomyocyte.

7. The method of claim 1, wherein said second cell is a fibroblast.

8. The method of claim 1, wherein said transcription inhibitor is 5,6-Dichloro-1-β-D-ribofuranosylbenzimidazole (DRB).

9. The method of claim 1, wherein said first cell and said second cell are each selected from the group consisting of a eukaryotic cell and a prokaryotic cell.

10. The method of claim 9, wherein said eukaryotic cell is a non-mammalian cell.

11. The method of claim 9, wherein said eukaryotic cell is a mammalian cell.

12. The method of claim 9, wherein said eukaryotic cell is a human cell.

13. The method of claim 2, wherein said phenotype-converting nucleic acid further comprises one or more exogenous nucleic acids selected from the group consisting of mRNA, siRNA, miRNA, hnRNA, tRNA, non-coding RNA and combinations thereof.

14. The method of claim 1, wherein said phenotype conversion comprises a change in one or more of gene expression, protein expression, immunological markers, morphology, physiology, synthesis of bioproducts, and membrane lipid composition.

15. The method of claim 14, wherein phenotype conversion comprises a change in expression of at least 100 genes.

16. The method of claim 14, wherein phenotype conversion comprises up-regulation of genes associated with chromosomal remodeling.

17. The method of claim 14, wherein at least about 5% of differentially expressed genes in said second cell change expression to a level observed for said first cell.

18. The method of claim 1, wherein said phenotype conversion persists for at least 2 weeks.

19. The method of claim 18, wherein said phenotype conversion persists for the lifetime of the cell.

* * * * *

UNITED STATES PATENT AND TRADEMARK OFFICE
CERTIFICATE OF CORRECTION

PATENT NO.        : 9,845,480 B2
APPLICATION NO.   : 14/880737
DATED             : December 19, 2017
INVENTOR(S)       : James Eberwine et al.

It is certified that error appears in the above-identified patent and that said Letters Patent is hereby corrected as shown below:

Please replace Column 1, Lines 21-28 as follows:
-- STATEMENT REGARDING FEDERALLY SPONSORED RESEARCH OR DEVELOPMENT
This invention was made with government support under grant numbers OD004117 and MH014654 awarded by the National Institutes of Health. The government has certain rights in the invention. --

Signed and Sealed this
Twelfth Day of February, 2019

Andrei Iancu
*Director of the United States Patent and Trademark Office*